US007736593B2

(12) United States Patent
Dastane et al.

(10) Patent No.: US 7,736,593 B2
(45) Date of Patent: Jun. 15, 2010

(54) DEVICE AND METHODS FOR COLLECTION OF BIOLOGICAL FLUID SAMPLE AND TREATMENT OF SELECTED COMPONENTS

(75) Inventors: Ajit N. Dastane, Bridgewater, NJ (US); Dimitrios Manoussakis, Wyckoff, NJ (US); Christopher A. Battles, Hamden, CT (US); Paul DiCesare, Easton, CT (US); Jeffrey Radziunas, Wallingford, CT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1374 days.

(21) Appl. No.: 10/912,263

(22) Filed: Aug. 5, 2004

(65) Prior Publication Data

US 2005/0059163 A1 Mar. 17, 2005

Related U.S. Application Data

(60) Provisional application No. 60/492,313, filed on Aug. 5, 2003.

(51) Int. Cl.
*G01N 1/18* (2006.01)

(52) U.S. Cl. ....................... 422/101; 604/403; 604/415; 436/177

(58) Field of Classification Search ....................... None
See application file for complete search history.

(56) References Cited

U.S. PATENT DOCUMENTS

| | | | | | |
|---|---|---|---|---|---|
| 3,929,646 | A | * | 12/1975 | Adler | 210/359 |
| 3,976,579 | A | * | 8/1976 | Bennett | 210/516 |
| 4,279,863 | A | | 7/1981 | Friehler | |
| 4,369,117 | A | * | 1/1983 | White | 210/782 |
| 5,511,558 | A | * | 4/1996 | Shepard et al. | 600/573 |
| 5,556,773 | A | * | 9/1996 | Yourno | 435/91.2 |
| 5,738,670 | A | * | 4/1998 | Grippi | 604/403 |
| 5,906,744 | A | | 5/1999 | Carroll et al. | |
| 6,001,087 | A | * | 12/1999 | Zurcher | 604/411 |
| 6,207,366 | B1 | * | 3/2001 | Suhadolnik | 435/4 |
| 6,551,777 | B1 | * | 4/2003 | Shuber et al. | 435/6 |
| 2003/0108447 | A1 | | 6/2003 | Yokoi et al. | |

FOREIGN PATENT DOCUMENTS

| | | | |
|---|---|---|---|
| EP | 0073551 | | 1/1982 |
| EP | 1106252 | * | 6/2001 |
| EP | 1106252 | A2 | 6/2001 |
| EP | 1516585 | A1 | 3/2005 |

* cited by examiner

*Primary Examiner*—Jill Warden
*Assistant Examiner*—Timothy G Kingan
(74) *Attorney, Agent, or Firm*—Mark Lindsey

(57) ABSTRACT

A collection device and a method for collecting a biological sample, particularly whole blood, includes a separating member to separate the whole blood into its components, and at least reagent positioned to selectively interact with a component of the separated sample. The reagent is able to selectively interact with the plasma/serum, and is prevented from contacting or interacting with the whole blood.

25 Claims, 38 Drawing Sheets

DEVICE AND METHODS FOR COLLECTION OF BIOLOGICAL FLUID SAMPLE AND TREATMENT OF SELECTED COMPONENTS

RELATED APPLICATIONS

This application claims priority to the provisional U.S. Patent Application No. 60/492,313 filed Aug. 5, 2003.

FIELD OF THE INVENTION

The present invention is directed to devices and methods for collecting and stabilizing a biological sample, particularly a whole blood sample, directly from a patient. More specifically, the present invention relates to sample collection devices having a stabilizing additive contained therein for stabilizing nucleic acids upon collection of biological samples and for inhibiting degradation during storage or transport thereof.

BACKGROUND OF THE INVENTION

Diagnostic tests may require separation of a patient's whole blood sample into components, such as plasma or serum (i.e., the lighter phase component) and red blood cells (i.e., the heavier phase component). For example, a plasma sample may be tested using known amplification techniques to monitor the HIV RNA viral load of HIV infected patients to diagnose and manage the disease. A patient's response to approved drugs, new drugs and combination drug therapies can be evaluated by monitoring the patient's HIV RNA viral load. In addition to the HIV virus, there are a number of other infectious diseases that would benefit from viral load monitoring, such as the Hepatitis C virus.

Currently, plasma viral monitoring is typically performed by drawing samples of whole blood by venipuncture through a cannula or needle attached to a syringe or an evacuated collection tube. Separation of the blood into plasma and other cellular components, or into serum and red blood cells is then accomplished by spinning of the syringe or tube in a centrifuge. Such techniques typically use a barrier that moves between the two phases of the sample being separated, thereby maintaining the component separation for subsequent examination of the individual components. Typically, the samples must then be transported to a different location, such as a laboratory, where personnel conduct specific tests on the samples. Generally, a considerable amount of time elapses between obtaining the sample and analyzing it. A common and recurring problem, therefore, is the maintenance of the biological sample in a manner that prevents degradation, alteration or destruction of essential materials during the manipulations and/or preparations preceding analysis of the biological sample.

Currently, blood samples are collected in EDTA tubes and spun to obtain plasma. The plasma samples are then shipped in primary or secondary tubes on ice or under refrigerated conditions for further analysis. The cold temperature shipping reduces vRNA degradation.

A need exists for a standard device designed to collect, process, and transport plasma samples for use with amplification technologies. Most preferably, the device should be able to assist in standardizing specimen handling, provide a closed system, isolate the plasma from the cellular components, produce minimal plasma dilution, and minimize interference with the nucleic acid testing.

SUMMARY OF THE INVENTION

The present invention is directed to a device for collecting a biological sample comprising a container having a reservoir portion for receiving the sample, a separating member disposed in the container to separate the sample into its components, and at least one reagent, e.g., a stabilizing agent such as for stabilizing nucleic acid, positioned in the container to selectively interact with at least one component of the separated sample. In one embodiment, the container is a tube having a first end and a second end, and the tube may be partially evacuated.

Typically the biological sample is whole blood. Preferably, the reagent is positioned to prevent interaction with the whole blood. More particularly, the reagent may be positioned to selectively interact with a plasma or serum component, while being substantially isolated from other components of the whole blood.

In one embodiment, the separating member is a mechanical separating element, and in an alternate embodiment, the separating member is a gel. The gel separating member may also be physically separated from the reagent.

The present invention is also directed to methods for collection and preparation of a plasma or serum specimen for subsequent testing, e.g., nucleic acid testing. The methods comprise providing a tube for receiving a whole blood sample. The tube comprises a top end and a bottom end, a separating member disposed within the tube to separate the sample into its components, and at least one reagent. e.g., a nucleic acid stabilizing agent. The methods further comprise collecting a whole blood sample into the tube, maintaining the whole blood sample separate from the reagent, separating plasma or serum from other blood components, and mixing the plasma or serum in the tube with the reagent.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. Numerous variations may be made by persons skilled in the art without departure from the spirit of the invention. The scope of the invention will be measured by the appended claims and their equivalents. In particular, while the invention is described with respect to the reagent being a nucleic acid stabilizing agent, other reagents are possible, such reagents able to provide a variety of functions other than, or in addition to, stabilization. One such alternative is a protein stabilizing reagent.

Although it is possible to use the present invention with any nucleic acid-containing biological sample, preferably the biological sample is any body fluid withdrawn from a patient. Most preferably, the biological sample is whole blood or a component thereof. Examples of other biological samples include plasma, serum, urine, bone marrow aspirates, cerebral spinal fluid, tissue, cells, feces, saliva and oral secretions, nasal secretions, bronchial lavage, cervical fluids, lymphatic fluid and the like.

Figure 1:
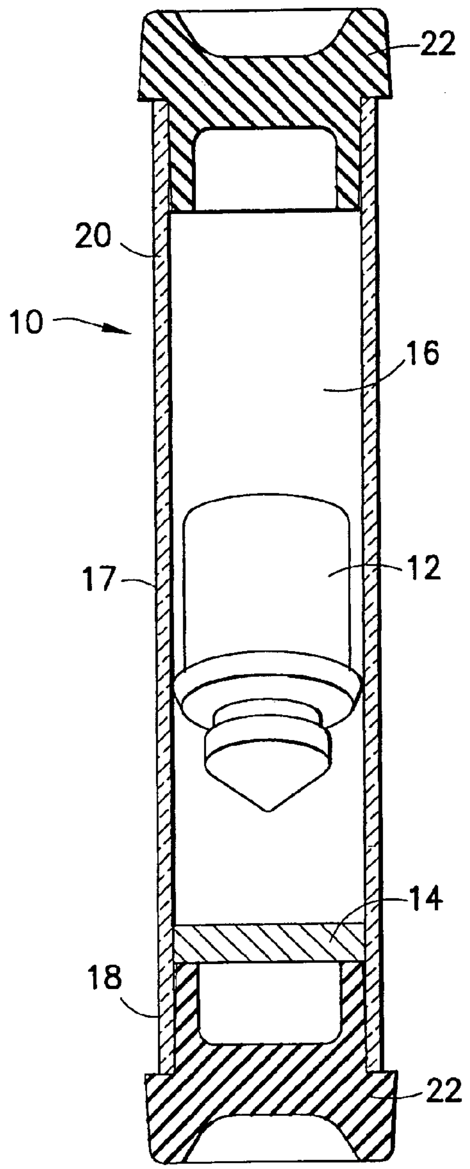
FIG. 1 is a cross-sectional view of a blood collection device according to one embodiment of the present invention.

Referring to the drawings in which like reference characters refer to like parts throughout the several views thereof, FIG. 1 depicts one embodiment of the invention, which generally comprises a sample collection container 10 having a separating member 12 (e.g., a mechanical separating element or a gel) for separating blood components and a stabilizing agent 14 for stabilizing the biological sample. Separating members are known in the art, as discussed in more detail below, and are provided with a density intermediate to the densities of the components to be separated. Upon centrifugation, the density relationships cause the separating member to move between those components. In the embodiment illustrated, container 10 comprises a hollow tube defining a reservoir or internal chamber 16 having a side wall 17 extending from an open bottom end 18 to an open top end 20. Separating member 12 is provided within the container chamber 16, and stabilizing agent 14 is provided within chamber 16 below separating member 12 toward bottom end 18. Separating member 12 serves to assist in separating components of the sample, for example, by centrifugation. Container 10 is dimensioned for collecting a suitable volume of biological fluid, preferably blood. A closure means 22 is provided for covering open ends 18, 20 to close container 10. For evacuated collection tubes, a tight-fitting, elastomeric plug is generally employed to contain the vacuum during the required storage periods. Preferably, closure 22 forms a seal capable of effectively closing container 10 and retaining a biological sample in chamber 16. The pressure in chamber 16 is preferably selected to draw a predetermined volume of biological sample into chamber 16. Preferably, closure 22 is made of a resilient material that is capable of maintaining the internal pressure differential between atmospheric pressure and a pressure less than atmospheric. Closure 22 is such that it can be pierced by a needle 26 or other cannula to introduce a biological sample into container 10 as known in the art. Preferably, closure 22 is resealable. Suitable materials for closure 22 include, for example, silicone rubber, natural rubber, styrene butadiene rubber, ethylene-propylene copolymers and polychloroprene.

Figure 2:
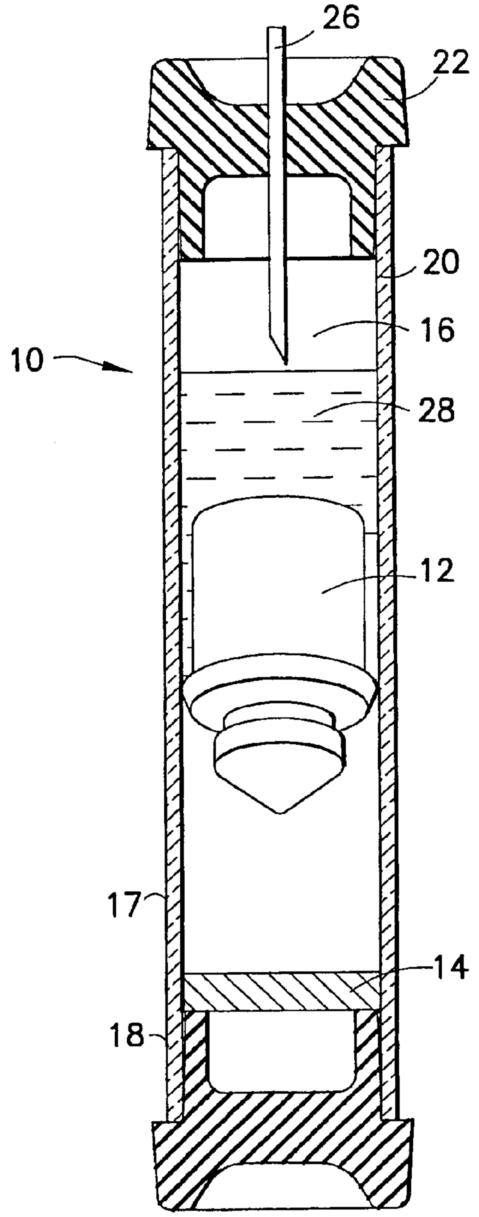
FIG. 2 is a cross-sectional view of the blood collection device of FIG. 1 during introduction of the sample into the device, but before centrifugation.
Figure 3:
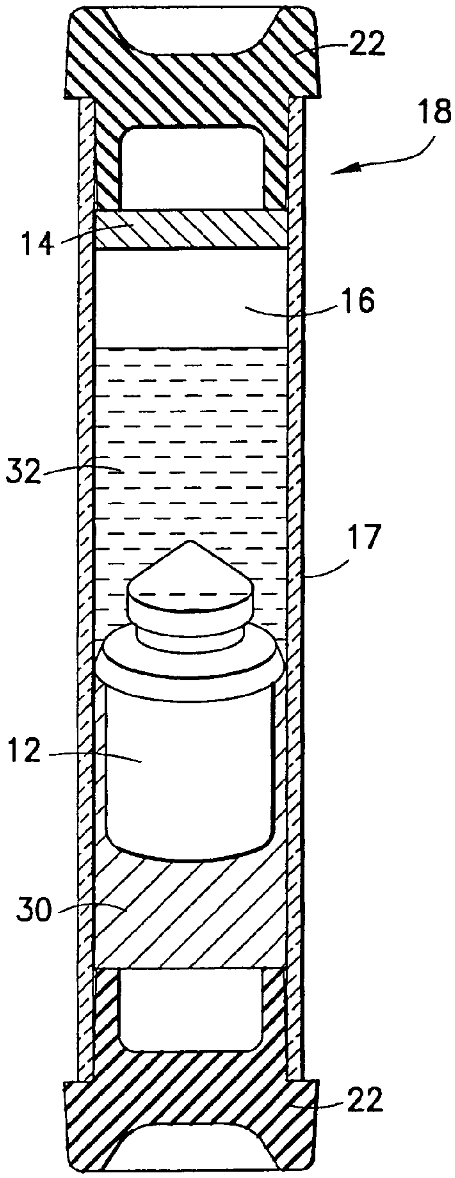
FIG. 3 is a cross-sectional view of the sample of FIG. 2 rotated through 180 degrees and after centrifugation facilitating separation into its components.

The methods of the present invention include obtaining a biological sample and introducing the sample into container 10. Various venipuncture devices have been developed to facilitate obtaining a biological sample, one type of these devices incorporates a needle assembly having a housing defining a chamber there within, wherein a single cannula with a notch or two separate cannulas that are pointed at both ends, are affixed to the housing. The intravenous (IV) end of the cannula is adapted for penetration of a patient's vein, and the non-patient end of the cannula has a sealable sleeve and adapted for penetration of a penetrable stop positioned within an evacuated container. For example, as shown in FIG. 2, a blood specimen sample 28 can be transferred into container 10 through the top end 20, and the specimen is initially kept within chamber 16 above separating member 12, as separating member 12 seals the specimen from bottom end 18 and prevents the sample from contacting stabilizing agent 14. After collection, the blood sample is separated into plasma and other cellular components, or into serum and red blood cells, such as by spinning of container 10 in a centrifuge. In a preferred embodiment, container 10 is placed into a centrifuge with bottom end 18 facing upwards, and the tube is centrifuged. Upon centrifugation separating member 12 elongates allowing flow around it. Because of the heavier density of the cellular components of the blood, these components move downward around the separator, while the separator moves upward due to its relative density. Upon cessation of centrifugation, the separator forms a seal between the components, such that the plasma or serum is adjacent the stabilizing agent. In this manner, the agent is substantially isolated from the cellular components of the blood throughout the procedure, as discussed in more detail below. Referring to FIG. 3, after centrifugation, the cellular component of the blood 30 remains below separating member 12 and the plasma or serum 32 remains above separating member 12 in contact with the stabilizing agent 14. After separation, the plasma or serum 32 is then typically mixed with the stabilizing agent 14, such as by inverting container 10 so that the stabilizing agent dissolves in, or otherwise interacts with, the plasma or serum fluid and degradation of the nucleic acids (or other elements) contained therein is minimized.

In preferred embodiments, the stabilizing agent is mixed with the plasma or serum soon after the sample is obtained and prior to storage or transfer. It has been found that collecting the biological sample directly from the patient, such as when collecting a whole blood sample, and immediately separating the plasma or serum from the cellular component of the blood and then introducing the stabilizing agent into the plasma substantially reduces, or may even prevent the degradation and/or fragmentation of nucleic acids that otherwise occurs when the sample is stored or transferred without combining it with a stabilizing agent. Advantageously, once the stabilizing agent is introduced into the plasma, there is no need to store or transfer the sample under refrigerated conditions.

In the embodiment shown in FIG. 1 sample collection container 10 comprises a double-ended tube suitable for plasma separation. Container 10 can be any collection device suitable for blood plasma or serum preparation. Suitable examples of container 10 include closed end tubes, single-wall tubes, and multi-layer tubes. An example of a suitable container 10 is disclosed in U.S. Pat. No. 3,919,085 to Ayres, which is hereby incorporated by reference in its entirety.

Container 10 can be made of glass, plastic or other suitable materials. Some preferred materials used to manufacture collection container 10 include polypropylene, polyethylene, polyethyleneterephthalate, polystyrene, polycarbonate and cellulosics. More expensive plastics such as polytetrafluoroethylene and other fluorinated polymers may also be used. In addition to the materials mentioned above, examples of other suitable materials include polyolefins, polyamides, polyesters, silicones, polyurethanes, epoxies, acrylics, polyacrylates, polysulfones, polymethacrylates, PEEK, polyimide and fluoropolymers such as PTFE Teflon®, FEP Teflon®, Tefzel®, poly(vinylidene fluoride), PVDF and perfluoroalkoxy resins. Glass products including silica glass may also be used to manufacture the collection devices. One exemplary glass product is PYREX® (available from Corning Glass, Coming, N.Y.). Ceramic collection devices can be used according to embodiments of the invention. Cellulosic products such as paper and reinforced paper containers can also be used to form collection devices according to the invention.

In one embodiment the reagent of the invention is any suitable nucleic acid stabilizing reagent that is able to inhibit the destruction of nucleic acids during storage or transfer of biological samples. These reagents include salts that precipitate the nucleic acid along with the cellular proteins. In most cases these salts tend to be dehydrating agents. The reagent stabilizes the plasma or serum sample to produce a stable composition that inhibits or prevents degradation and/or fragmentation of nucleic acids. A variety of nucleic acid stabilizing agents known in the art may be used. Suitable examples include, sulfate salts like ammonium sulfate, ammonium bisulfate, cesium sulfate, cadmium sulfate, cesium iron (II) sulfate, cobalt (II) sulfate, copper (II) sulfate, lithium sulfate, magnesium sulfate, manganese sulfate, potassium sulfate, sodium sulfate, and zinc sulfate. At least one suitable stabilizing agent is commercially available under the trade name RNAlater™ from Ambion, Inc. As noted above, other reagents performing any desired action are also possible, where one wishes to avoid contact between the cellular components and the reagent. One such possible reagent is a protein stabilizer.

As noted above, other reagents performing any desired action are also possible, where one wishes to avoid contact between the cellular components and the reagent. For example, where a reagent does damage to cells in whole blood, it is desirable to keep the reagent away from the whole blood sample until the serum or plasma is separated out.

The reagent may be in any suitable form including, but not limited to, a solution, suspension or other liquid, a pellet, a tablet, a capsule, a spray-dried material, a freeze-dried material, a powder, a particle, a gel, crystals or a lyophilized material. The reagent may be encapsulated to prevent undesirable interactions between the reagent and other elements in the container, such as a gel separator. Capsule materials that dissolve upon sample collection are well known in the art. Further, the stabilizing agent may be mixed with other excepients to enhance its dispersion/solubility in the biological fluid and/or to improve its stability during manufacturing and subsequent handling/transport of the finished product. For example, some such materials include polyvinylpyrollidone (PVP), microcrystalline celluloses such as AVICEL and the like. In the embodiment reflected in FIG. 1, it is useful to have the reagent in solid form, such as a tablet, with the tablet placed adjacent the bottom end 18 of container 10.

It is possible for the collection device to be pre-loaded with the stabilizing agent, preferably by the manufacturer, and packaged in a ready-to-use form. Typically, the packaged collection device is sterile and is also packaged in sterile packaging materials. The reagent is preferably preloaded into the container and located remotely from the point of entry of the whole blood or other biological sample, and the separating member is interposed therebetween so as to prevent contact with whole or unseparated blood. For example in this first embodiment, as seen in FIG. 2, stabilizing agent 14 is positioned below the separating member 12 and opposite from the intake of the whole blood 30 or other biological sample.

Providing a separating member in plasma or serum tubes and preventing the stabilizing agent from contacting the whole blood is particularly advantageous. Specifically, when whole blood contacts a stabilizing agent, many agents tend to cause cell lysing. Such lysing releases all the cellular components normally held within the cell and thereby has an adverse effect on obtaining the desired quantity or type of nucleic acids (DNA, RNA, vRNA, etc.). Separating member 12 advantageously permits the stabilizing agent to selectively contact or interact with only the plasma or serum component of the blood sample, while preventing the stabilizing agent from contacting or interacting with the cellular component of the blood sample. Once the stabilizing agent and plasma are mixed, the nucleic acids in the plasma or serum are stabilized and there is no need to store or ship the sample under refrigerated conditions.

The stabilizing agent may be loaded into the collection device of this embodiment by any number of methods. One exemplary method may be to wedge a tablet of stabilizing agent into the device such that it does not move under centrifugal force. Another method may involve coating the stabilizing agent onto a carrier, which in turn is wedged in the device. Additional methods for providing the collection device with the stabilizing agent are also possible. The quantity and location of the stabilizing agent are determined by several variables, including the mode of application, the specific stabilizing agent used, the internal volume and internal pressure of the collection device, and the volume of the biological sample drawn into the container.

Referring again to FIG. 1, it is possible for separating member 12 to comprise a mechanical separator device. The mechanical separator device desirably isolates the plasma/serum from the cells/clot of the blood sample in container 10 by serving as a buoyancy separation device. Useful mechanical separators are found, for example, in U.S. Pat. Nos. 6,516,953; 6,406,671; 6,409,528; and 6,497,325, the contents of which are hereby incorporated by reference in their entirety. During collection, the mechanical separator provides a physical seal between two sections within the reservoir, thereby precluding whole blood from interacting with the stabilizing agent. During centrifugation, centrifugal forces cause elongation of the separating member and thereby reduce the outer diameter of the sealing portion of the separator and this allows movement of the separator to a location (based on density) between the plasma or serum and the other components, and associated flow of blood components around the exterior of the separator. Upon cessation of centrifugation, the separator again reseals against the inner tube walls, thereby separating the blood components.

Figure 4:
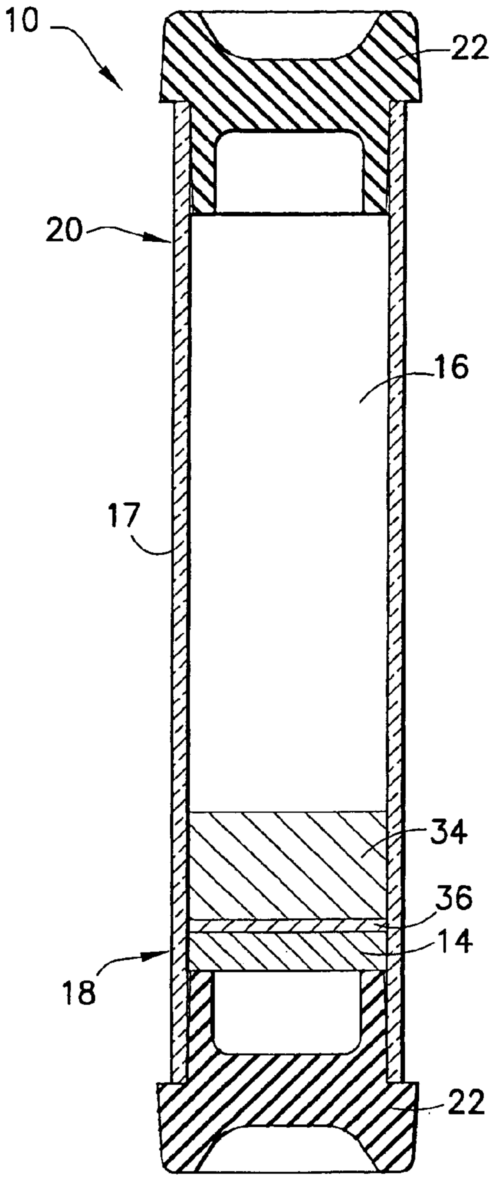
FIG. 4 is a cross-sectional view of an alternate embodiment of a blood collection device of the present invention having a gel separating member.

Referring to FIG. 4, an alternate embodiment is shown wherein the separating member comprises a gel 34. The gel is desirably a thixotropic polymeric gel formulation. The gel may be a homopolymer or a copolymer and may include silicone-based gels such as, for example, polysiloxanes, or organic hydrocarbon-based gels such as, for example, polyacrylics, polyesters, polyolefins, oxidized cis polybutadienes, polybutenes, blends of epoxidized soybean oil and chlorinated hydrocarbons, copolymers of diacids and propandiols, hydrogenated cyclopentadienes and copolymers of alpha-olefins with dialkylmaleates. The gel desirably isolates the plasma/serum from the cells/clot of the blood sample in the tube by serving as a density separation medium as known in the art. An example of a single-ended plasma preparation tube utilizing gel is disclosed in U.S. Pat. No. 5,906,744 to Carroll et al., which is hereby incorporated by reference in its entirety. In the case of a gel separating material, it may be desirable to also provide a physical or chemical separation between the stabilizing agent and the gel. For example, if portions of the agent are incorporated into or react with the gel, the effectiveness of the stabilizing agent may be reduced. As shown in FIG. 4, a barrier partition 36 that is soluble by plasma may be used to separate the stabilizing agent 14 from gel 34. A capsule, as discussed above, may alternatively be used to provide a chemical barrier between the stabilizer and the gel. During collection the gel separator along with the barrier partition provides a physical seal between two sections within the reservoir, thereby precluding whole blood from interacting with the stabilizing agent. Other separating members e.g. filters or manual separation elements, are known in the art and may also be suitable in the invention.

Generally, the separating member partitions the reservoir into first and second sections, and one of the first and second sections comprises the reagent. The other section (i.e., the one not comprising the reagent) may comprise another agent, e.g. for clot inhibition or clot activation. The clot activating agent may be silica based. Alternatively, the clot activating agent may be kaolin or thrombin. The clot inhibiting agent may include hirudins, hirudin derivatives, chelating agents, or chelating agent derivatives. Specific clot inhibiting agents include citrate, ethylenediaminetetraacetic acid, heparin, CPAD, CTAD, CPDA-1, CP2D, potassium oxalate, sodium fluoride or ACD.

FIGS. 5 to 15 show various embodiments of the invention involving a tube having an open top end and a closed bottom end. In such embodiments, the blood is typically drawn into the same end from which the treated plasma or serum sample is to be recovered. This requires locating the reagent at or proximate the open end, and using a reagent release mechanism (advantageously a passive reagent release mechanism)

to bring the reagent into contact with the desired portion of the blood sample. The reagent release mechanism thus keeps the reagent from coming into contact with the whole blood sample during blood collection and separation, but allows the reagent to mix with the desired components of the separated (e.g. post-centrifuged) sample. A passive reagent release mechanism will be activated by the separation process as opposed to a manually activated reagent release mechanism, which requires an extra manual step (such as twisting a closure or pressing a button) in order to bring the reagent into contact into with the plasma or serum sample.

Figure 5A:
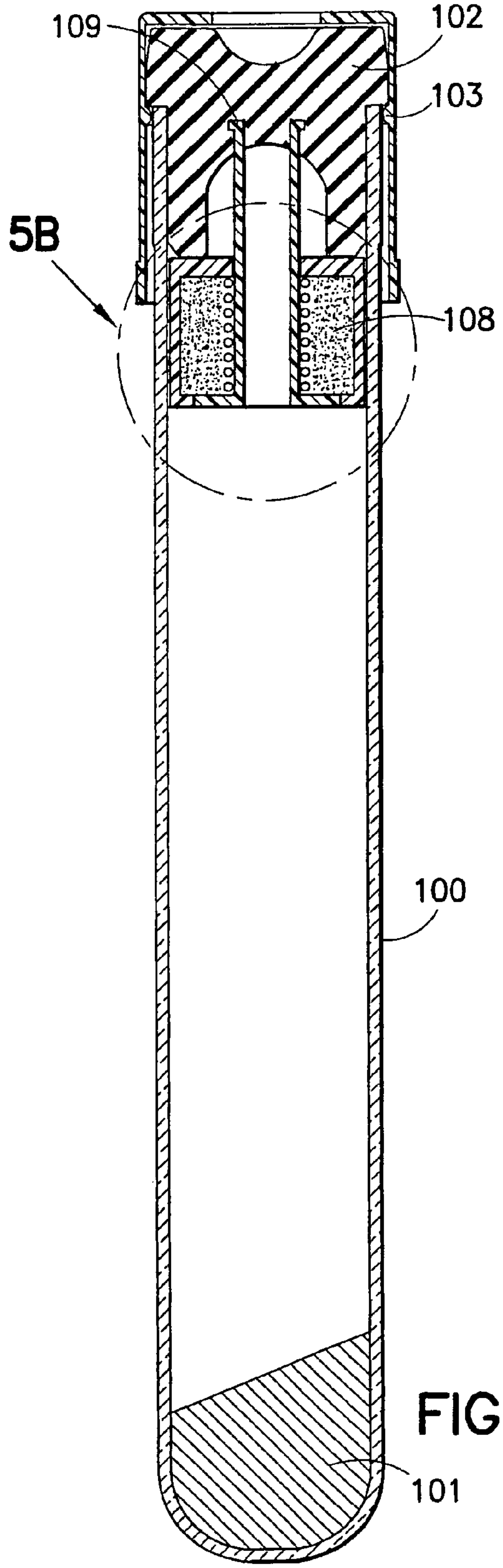
FIG. 5A is a cross-sectional view of an alternate embodiment of a blood collection device of the present invention having a gel separating member.
Figure 5B:
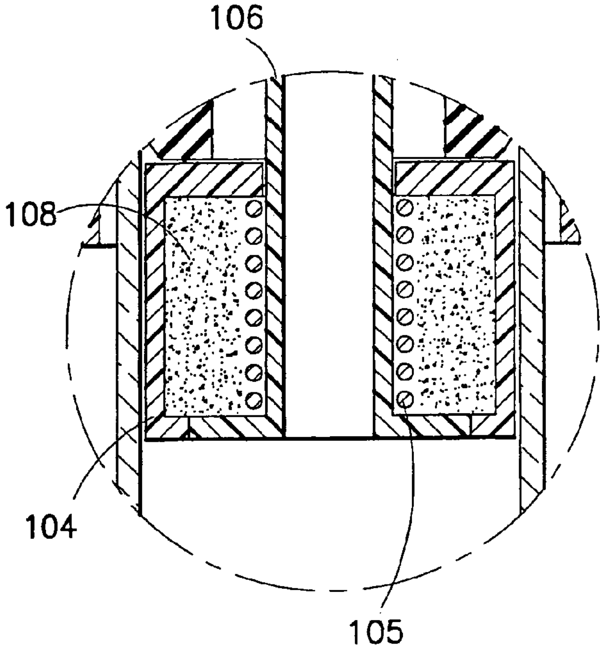
FIG. 5B is a magnified cross-sectional view of the reagent release mechanism of the blood collection device of FIG. 5A.
Figure 5C:
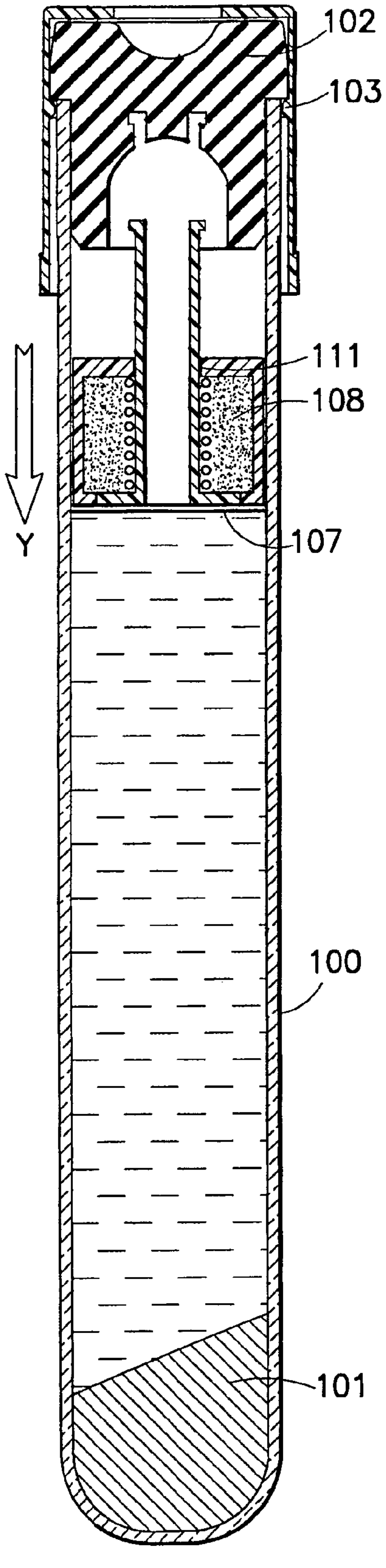
FIG. 5C is a cross-sectional view of the blood collection device of FIG. 5A containing the whole sample during the initial stages of centrifugation.
Figure 5D:
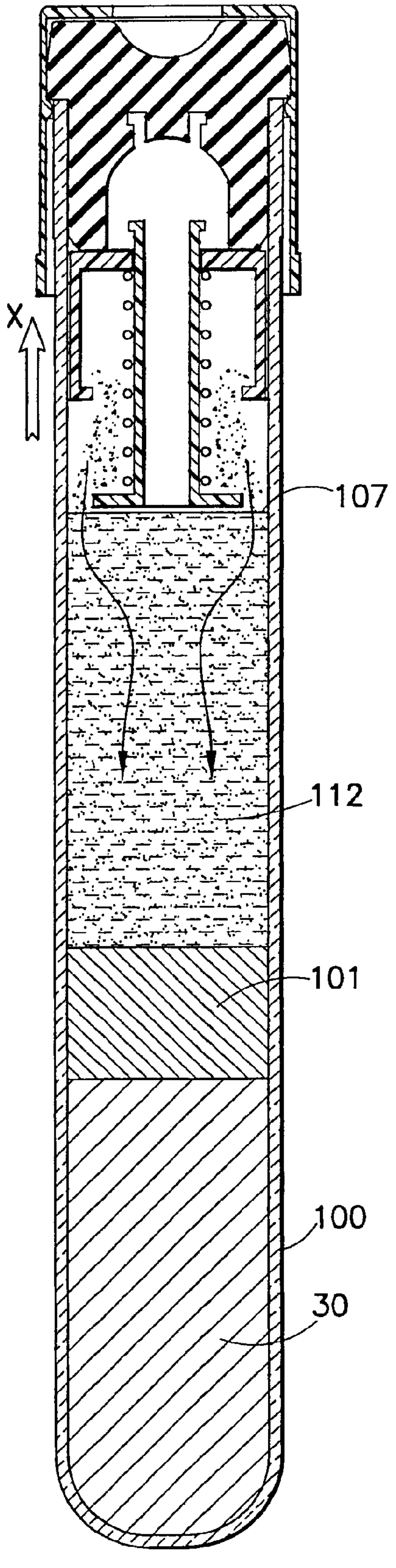
FIG. 5D is a cross-sectional view of the blood collection device of FIG. 5A after centrifugation facilitating separation into its components and activation of the reagent release mechanism.

FIGS. 5A, B, C and D show a tube 100 having an open top end and a closed bottom end containing a gel separating member 101. FIGS. 5A and 5B show the reagent 108 is contained within a cup 104, which seals against the tube closure 102. A precompressed spring 105 is located between the cup 104 and the fill tube 106 and is held in state by the presence of the closure 102. The cup is sealed using a flange 109 on the fill tube 106. The whole blood sample is introduced into the tube 100 through the closure 102 and via the fill tube 106. FIG. 5C shows that during centrifugation the entire reagent assembly 111 launches from the closure in the direction Y and floats on the surface of the plasma/blood 107. However the reagent cup 104 remains sealed using either differential buoyancy or by selection of a spring that remains partially coiled during centrifugation. FIG. 5D shows that after centrifugation is complete, the spring 105 lifts up the reagent cup 104 in the direction of X, thereby allowing the reagent 108 to enter and mix with the separated plasma 112 (It should be noted that 112 can also represent the separated plasma and reagent mixed together as seen clearly in FIGS. 5D, 6D, 8F).

Figure 6A:
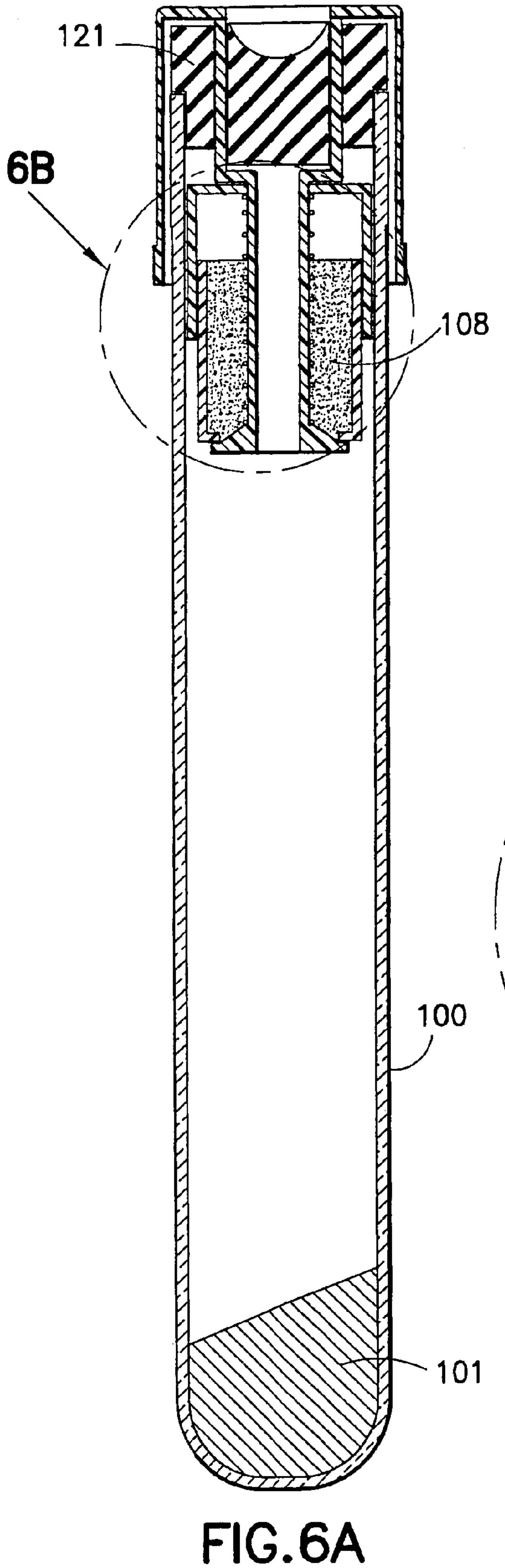
FIG. 6A is a cross-sectional view of an alternate embodiment of a blood collection device of the present invention having a gel separating member.
Figure 6B:
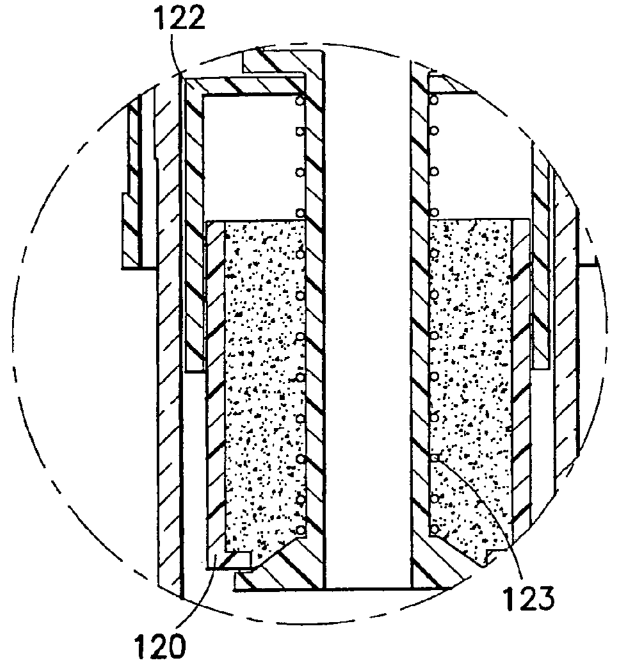
FIG. 6B is a magnified cross-sectional view of the reagent release mechanism of the blood collection device of FIG. 6A before centrifugation.
Figures 6C, 6D, 6E:
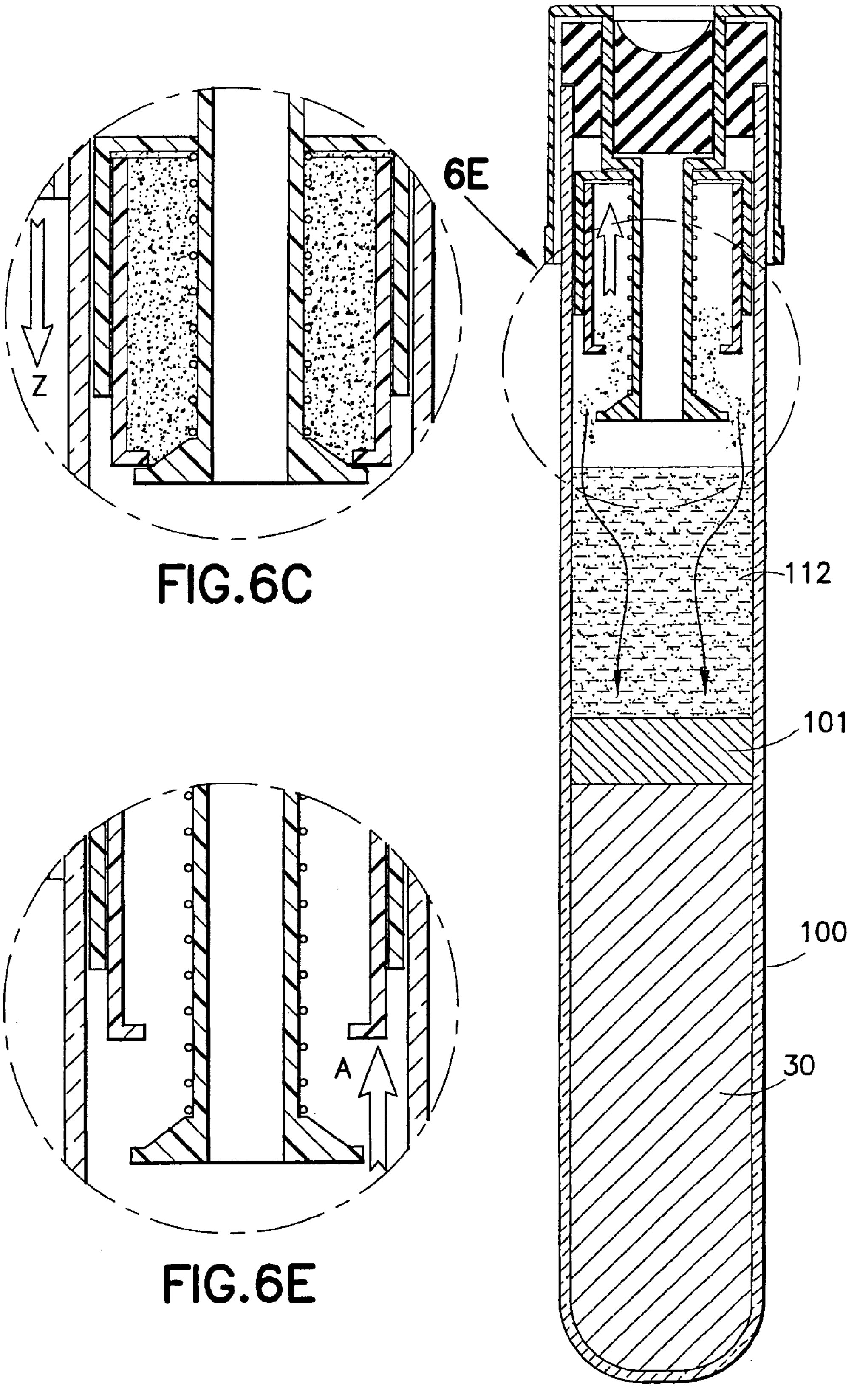
FIG. 6C is a magnified cross-sectional view of the reagent release mechanism of the blood collection device of FIG. 6A during centrifugation.
FIG. 6D is a cross-sectional view of the blood collection device of FIG. 6A after centrifugation facilitating separation into its components and activation of the reagent release mechanism.
FIG. 6E is a magnified cross-sectional view of the reagent release mechanism of the blood collection device of FIG. 6A after centrifugation.

FIGS. 6A to E show a tube 100 having an open top end and a closed bottom end containing a gel separating member 101. FIGS. 6A and B show the reagent 108 contained within a telescoping cup 120, suspended from the underside of the tube closure 121 before centrifugation. FIG. 6C shows that the upper section or sliding cover 122 of the reagent cup is drawn down in the direction Z during centrifugation, overcoming the force exerted by the compression spring 123. FIGS. 6D and 6E show that when the centrifugation is complete, the friction between the two-cup sections 120 and 122 allows the spring 123 to raise both sections of the cup 120 and 122 in the direction A, thereby opening a path for the reagent 108 to escape and mix with the separated plasma 112.

Figure 7A:
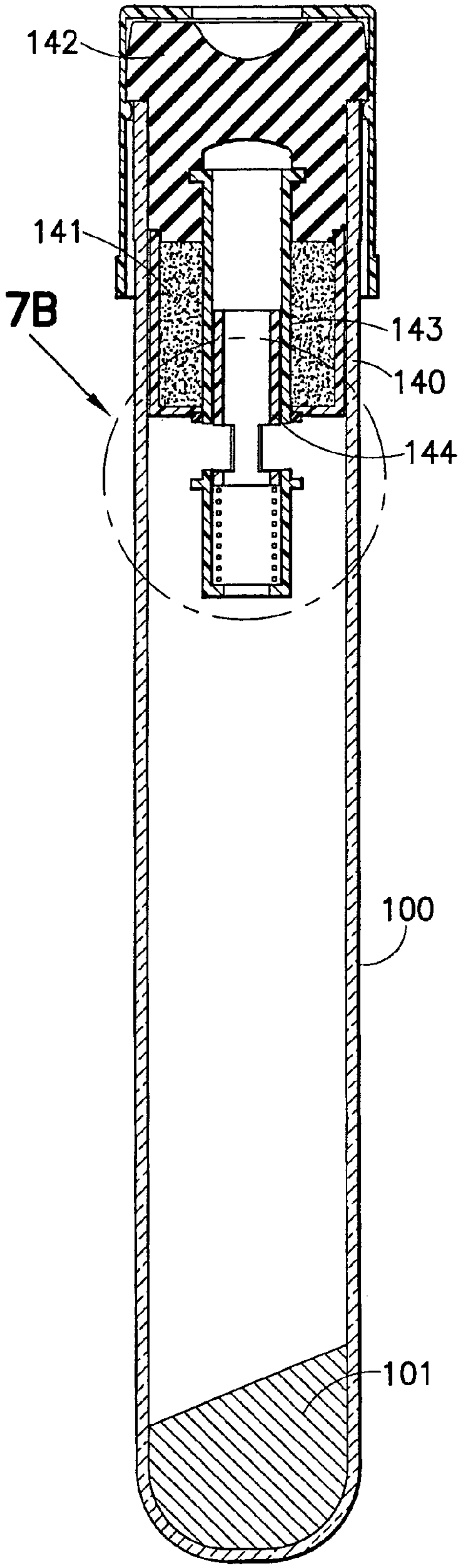
FIG. 7A is a cross-sectional view of an alternate embodiment of a blood collection device of the present invention having a gel separating member.
Figure 7B:
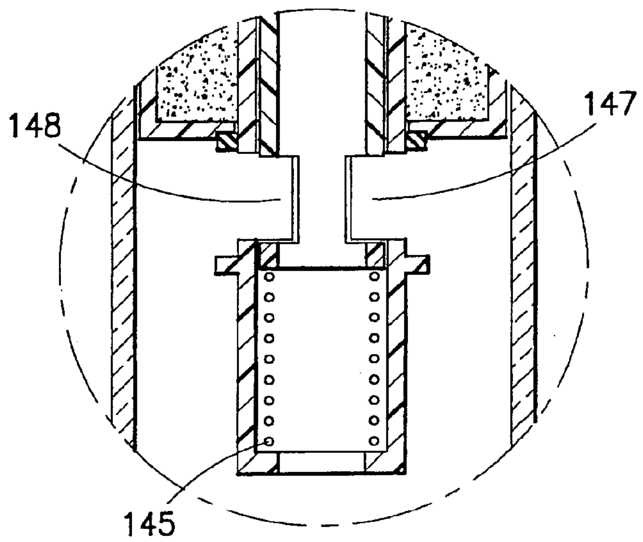
FIG. 7B is a magnified cross-sectional view of the reagent release mechanism of the blood collection device of FIG. 7A before centrifugation.
Figure 7C:
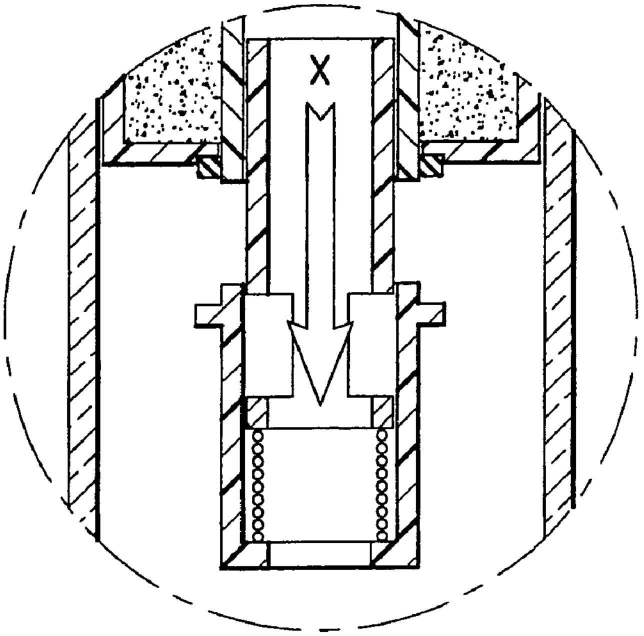
FIG. 7C is a magnified cross-sectional view of the reagent release mechanism of the blood collection device of FIG. 7A during the initial stage of centrifugation.
Figure 7D:
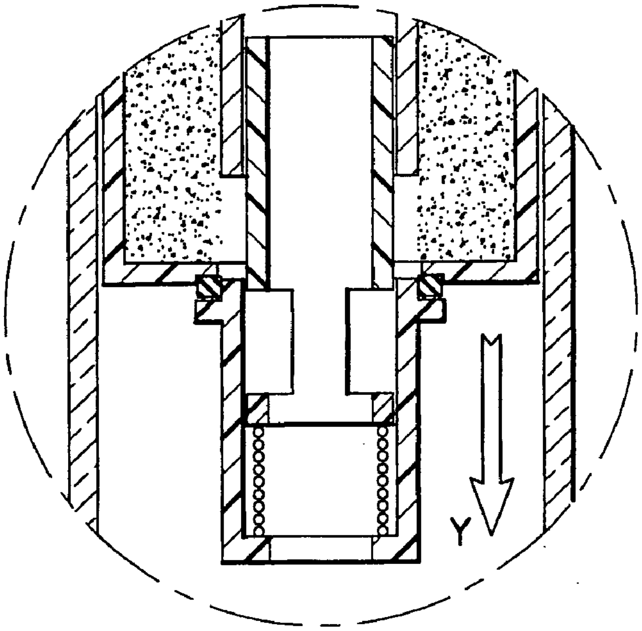
FIG. 7D is a cross-sectional view of the reagent release mechanism of the blood collection device of FIG. 7A during the final stage of centrifugation.
Figure 7F:
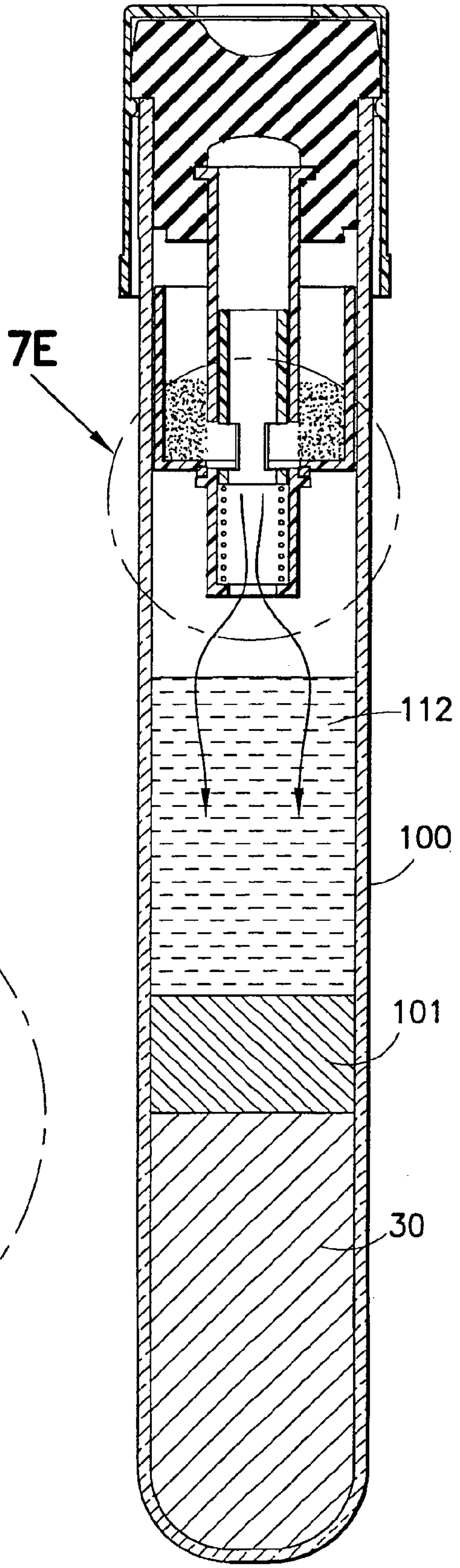
FIG. 7F is a cross-sectional view of the blood collection device of FIG. 7A after centrifugation facilitating separation into its components and activation of the reagent release mechanism.
Figure 7E:
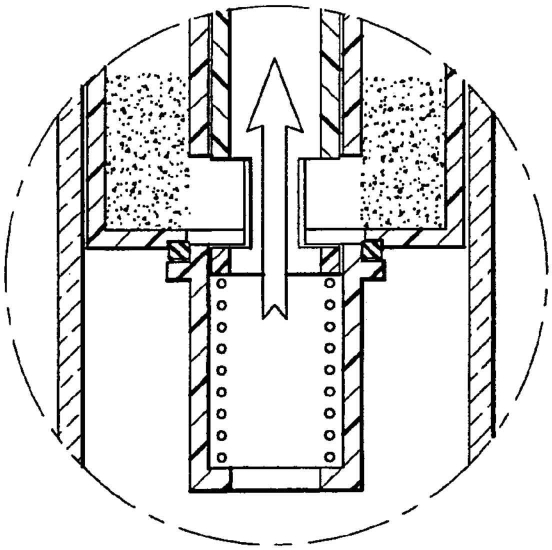
FIG. 7E is a cross-sectional view of the reagent release mechanism of the blood collection device of FIG. 7A after centrifugation.

FIGS. 7A to F show a tube 100 having an open top end and a closed bottom end containing a gel separating member 101. FIGS. 7A and B show the reagent 141 contained within a cup 140 engaged with the tube closure 142 and sealed against the fill tube 143. An access tube 144 is located within the fill tube 143 and is spring 145 loaded in a nominal position where complementary windows in the fill 147 and access tubes 148 are aligned. FIG. 7C shows that during centrifugation, the access tube 144 is forced downward in the direction of X against the compression spring 145, thereby occluding the windows. FIG. 7D then shows that at this point during centrifugation the reagent cup 140 launches in the direction of Y from the tube closure 142 and positions itself at the window 147 in the fill tube. FIGS. 7E and 7F show that after centrifugation the access tube 144 is returned to its nominal state by the compression spring 145, realigning the windows 147 and 148 and allowing the reagent 141 to exit into the separated plasma 112.

Figure 8A:
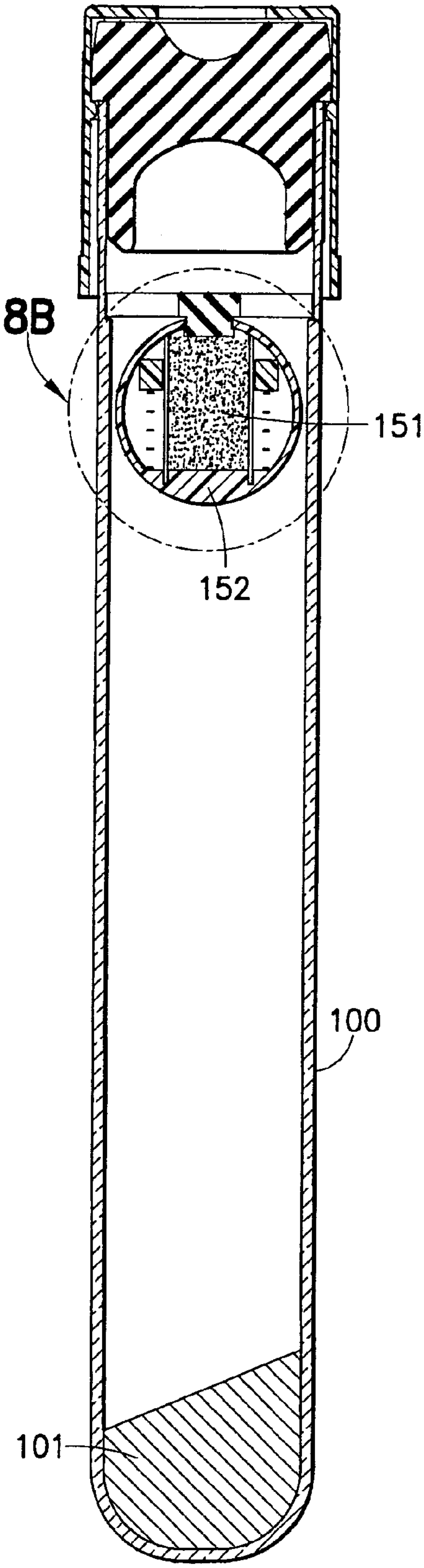
FIG. 8A is a cross-sectional view of an alternate embodiment of a blood collection device of the present invention having a gel separating member.
Figure 8B:
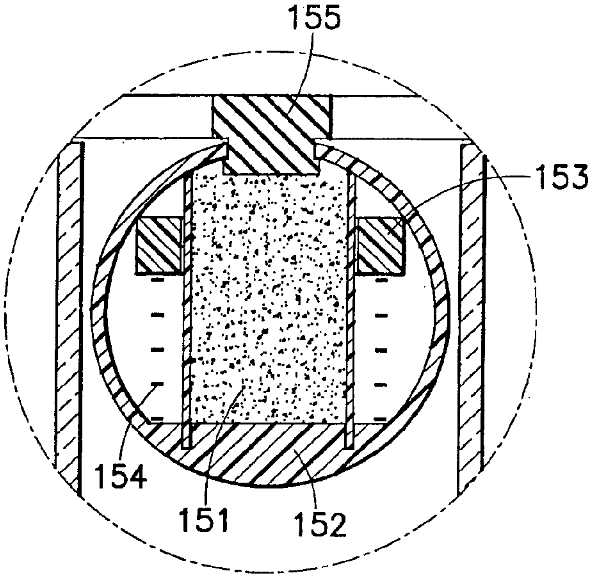
FIG. 8B is a magnified cross-sectional view of the reagent release mechanism of the blood collection device of FIG. 8A before centrifugation.
Figure 8C:
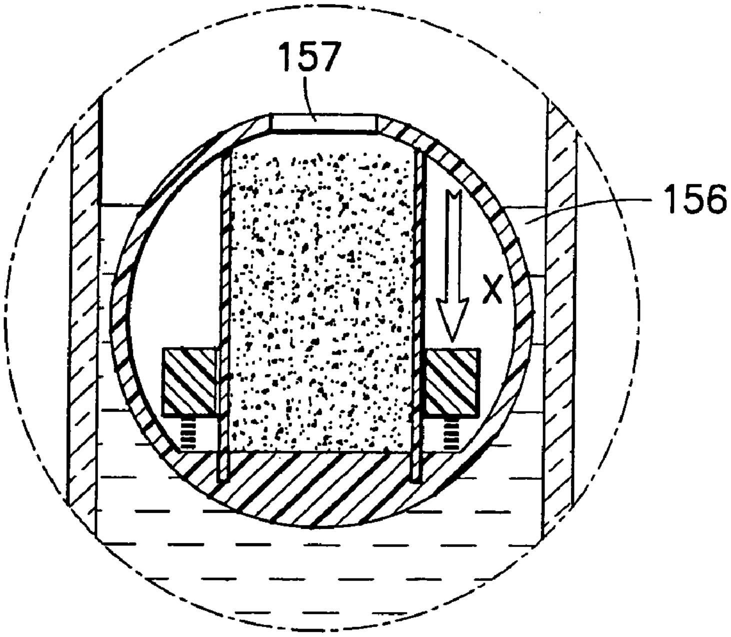
FIG. 8C is a magnified cross-sectional view of the reagent release mechanism of the blood collection device of FIG. 8A during centrifugation.
Figure 8D:
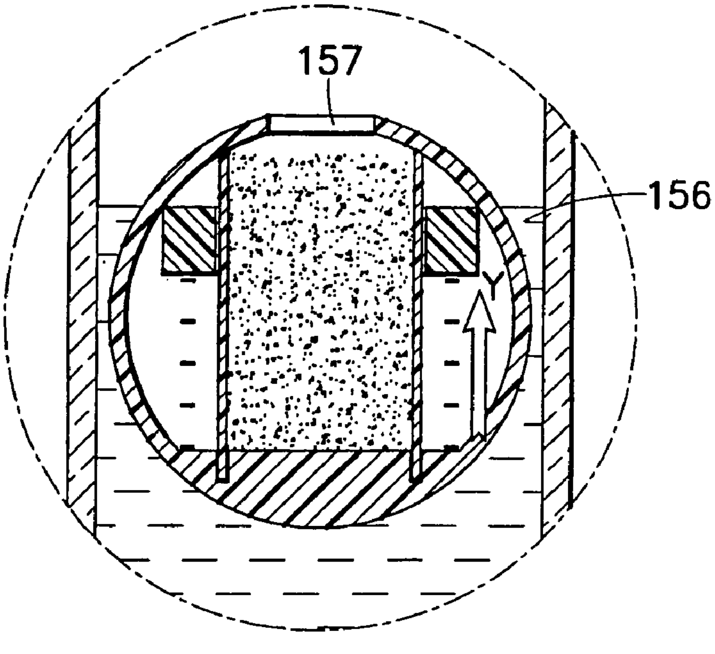
FIG. 8D is a magnified cross-sectional view of the reagent release mechanism of the blood collection device of FIG. 8A immediately after centrifugation.
Figure 8E:
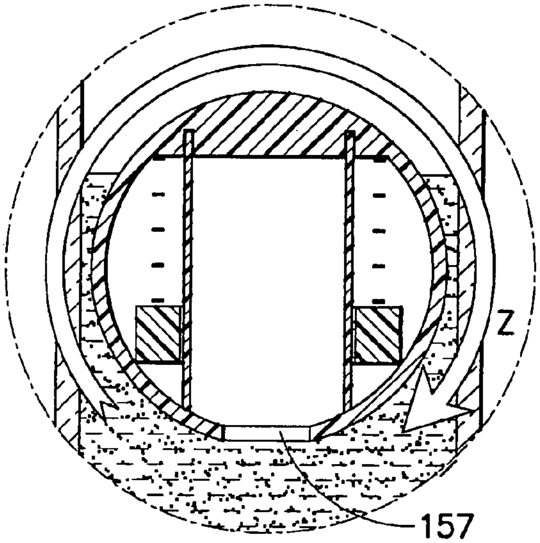
FIG. 8E is a magnified cross-sectional view of the reagent release mechanism of the blood collection device of FIG. 8A after centrifugation.
Figure 8F:
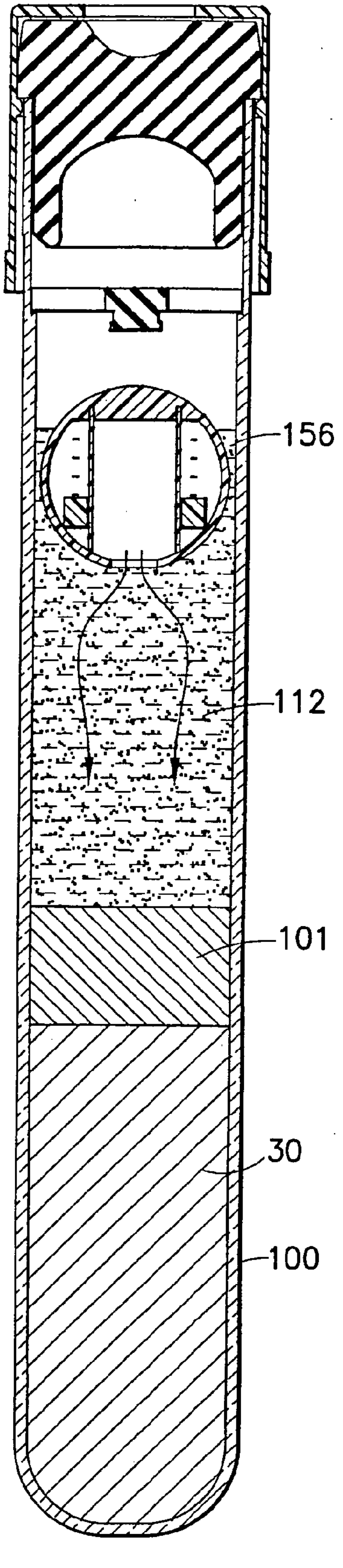
FIG. 8F is a cross-sectional view of the blood collection device of FIG. 8A after centrifugation facilitating separation into its components and activation of the reagent release mechanism.

FIGS. 8A to F show a tube 100 having an open top end and a closed bottom end containing a gel separating member 101. FIGS. 8A and B show the reagent 151 contained within a hollow ball 152. Inside the hollow ball 152 is a ballast weight 153, which is biased towards the tube closure by a light spring 154. FIG. 8C shows that during centrifugation the hollow ball 152 releases from the seal 155, as a result of the ballast weight 153 being drawn to the bottom of the ball 152 in direction X and floats on the surface of the plasma/blood 156 as a result of the buoyancy of the hollow ball 152. The center of gravity being shifted to the bottom of the hollow ball 152 by the moving ballast weight 153 causes the ball 152 to float stably with the reagent access hole 157 above the fluid surface 156. After centrifugation, FIG. 8D shows that the ballast weight 153 will rise again in direction Y as a result of the spring 154 to its original resting place, above the center of buoyancy. This will cause the hollow ball 152 to become unstable and it will roll in direction Z as shown in FIG. 8E and F, releasing reagent 151 into the separated plasma 112.

Figure 9A:
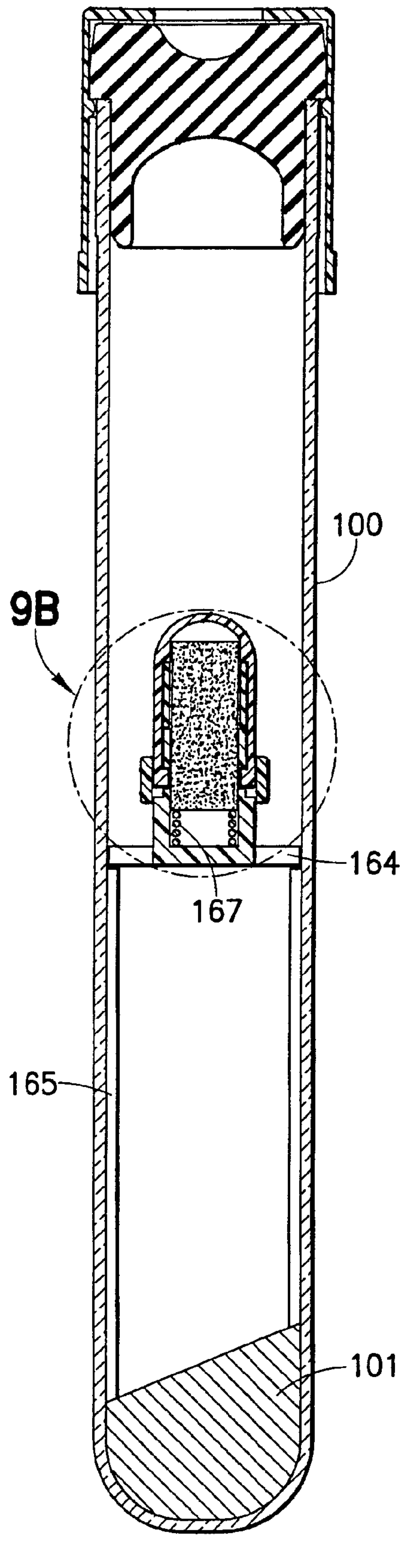
FIG. 9A is a cross-sectional view of an alternate embodiment of a blood collection device of the present invention having a gel separating member.
Figure 9B:
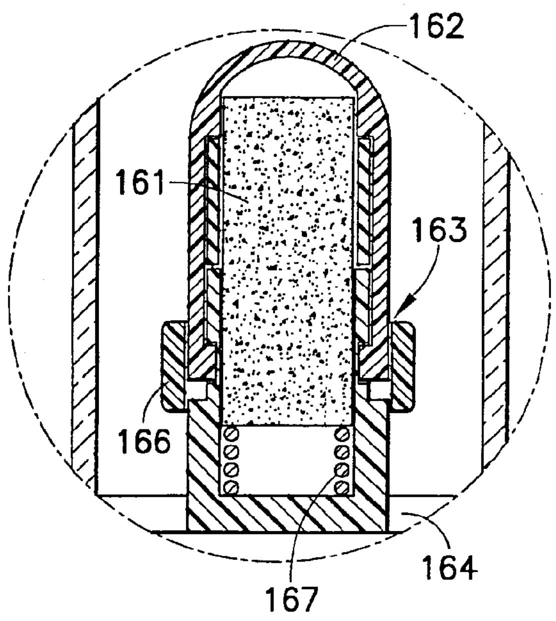
FIG. 9B is a magnified cross-sectional view of the reagent release mechanism of the blood collection device of FIG. 9A before centrifugation.
Figure 9C:
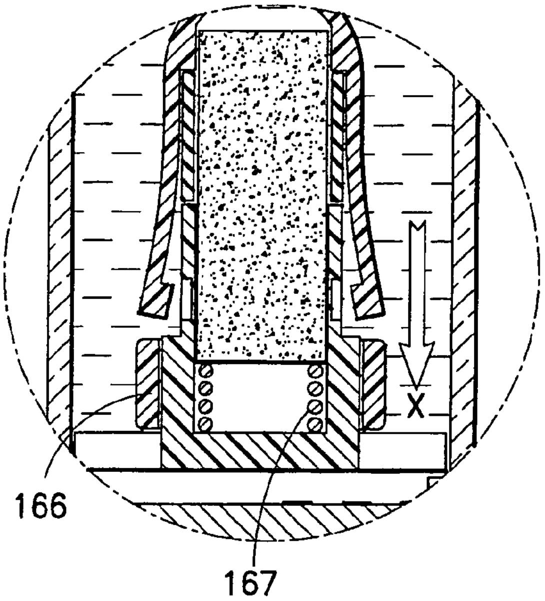
FIG. 9C is a magnified cross-sectional view of the reagent release mechanism of the blood collection device of FIG. 9A during centrifugation.
Figure 9D:
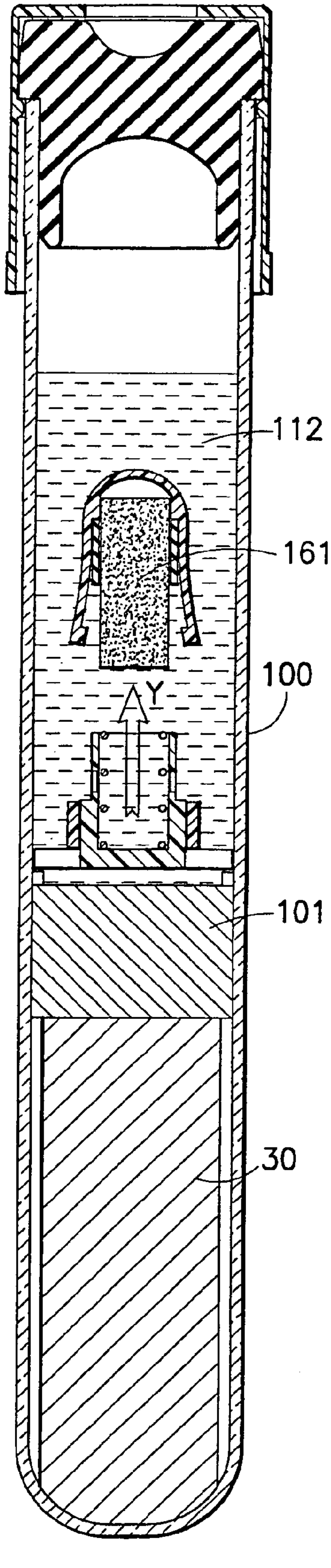
FIG. 9D is a cross-sectional view of the reagent release mechanism of the blood collection device of FIG. 9A after centrifugation facilitating separation into its components and activation of the reagent release mechanism.

FIGS. 9A to D show a tube 100 having an open top end and a closed bottom end containing a gel separating member 101. FIGS. 9A and B show the reagent 161 housed under a cap 162 with integral spring fingers 163 before centrifugation. The reagent housing is mounted on a support plate 164 which in turn is supported by internal ribs 165 within the bottom half of the tube. The spring fingers 163 are held in a locked position by the locking ring 166. FIG. 9.C shows that during centrifugation, the locking ring 166 moves in direction X, sliding off the spring fingers 163, allowing them to open, freeing the reagent cap 161. However the reagent 161 remains isolated as the gravitational forces still acting on the cap 161 prevent its release while under centrifugation. FIG. 9.D shows that after centrifugation the reduction of gravitational forces allows the internal spring 167 to eject the reagent cap 162 in direction Y, allowing the reagent 161 to mix with the separated plasma 112.

Figure 10A:
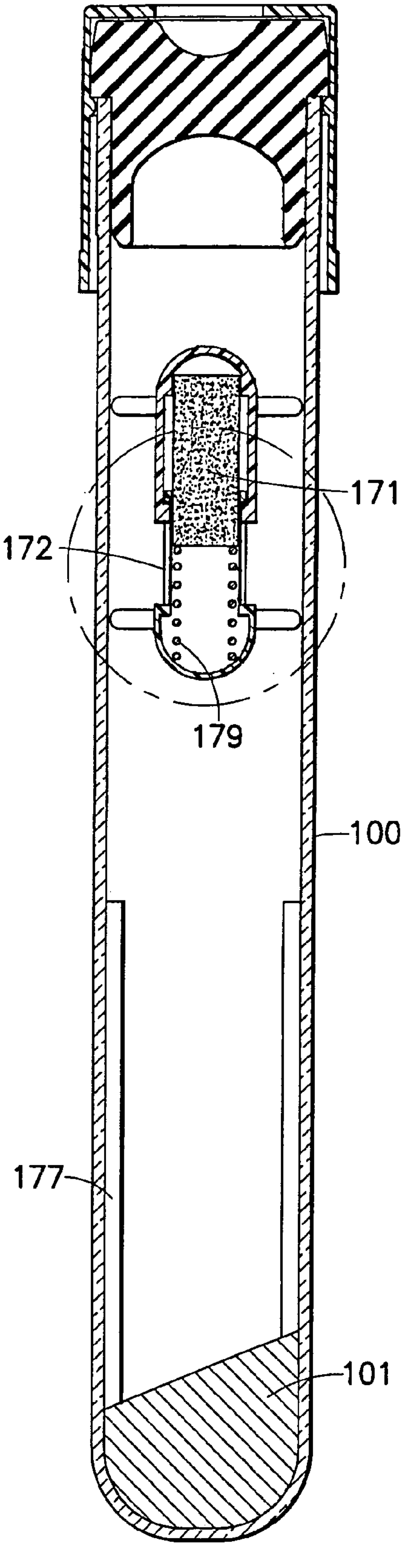
FIG. 10A is a cross-sectional view of an alternate embodiment of a blood collection device of the present invention having a gel separating member.
Figure 10B:
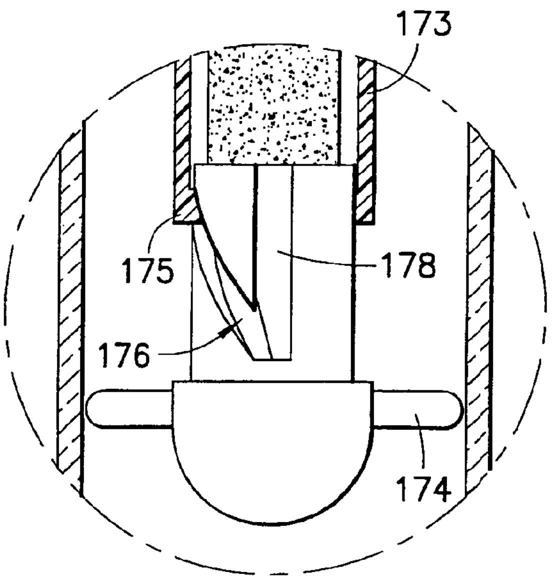
FIG. 10B is a magnified cross-sectional view of the reagent release mechanism of the blood collection device of FIG. 10A before centrifugation.
Figure 10C:
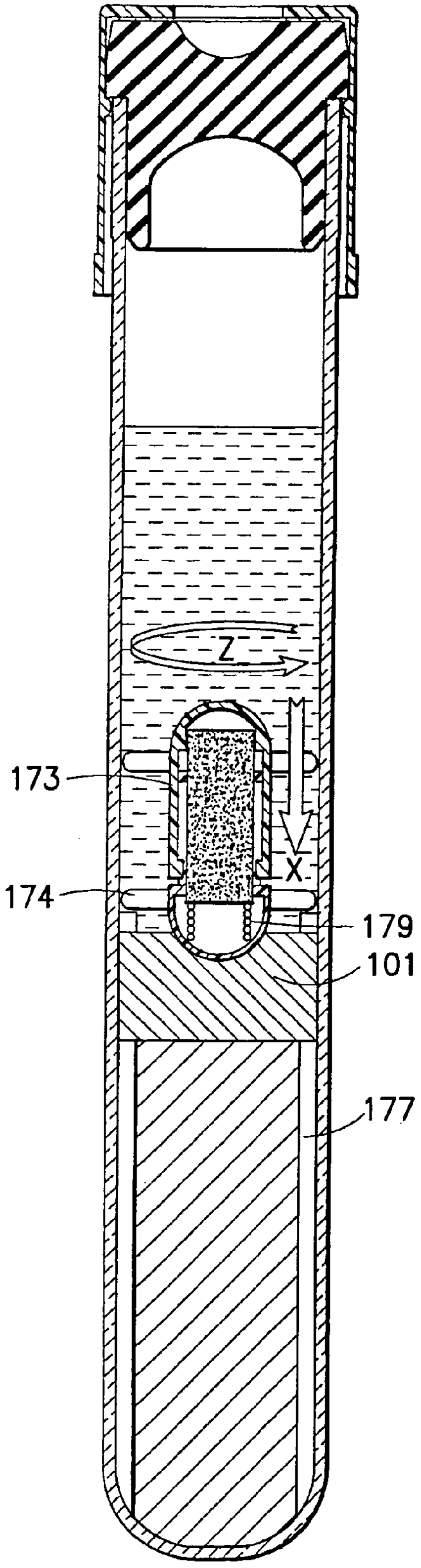
FIG. 10C is a cross-sectional view of the blood collection device of FIG. 10A during centrifugation.
Figure 10D:
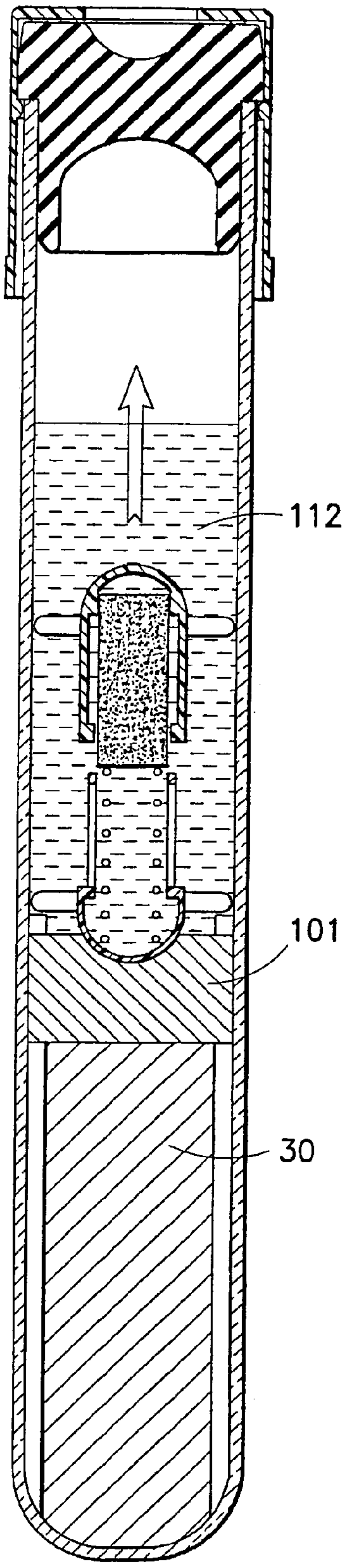
FIG. 10D is a cross-sectional view of the reagent release mechanism of the blood collection device of FIG. 10A after centrifugation facilitating separation into its components and activation of the reagent release mechanism.

FIGS. 10A to D show a tube 100 having an open top end and a closed bottom end containing a gel separating member 101. FIGS. 10A and B show the embodiment before centrifugation, the reagent 171 contained within a two-piece capsule 172. The capsule 172 consists of the cap 173 and the lower housing 174, the cap 173 has two teeth 175 which engage a cam track 176 on the lower housing 174. FIG. 10C shows that during centrifugation the capsule 172 sinks down in direction X through the sample until it contacts support ribs 177 on the inner surface of the tube, at which point the lower housing 174 stops moving. However the cap 173 continues to advance, following the helical cam track 176, twisting in direction Z as it progresses. FIG 10D shows that after centrifugation, the teeth 175 on the cap 173 are now located in exit tracks 178 in the lower housing 174. A spring 179 then ejects the cap 173 and the reagent 171 into the separated plasma 112.

Figure 11A:
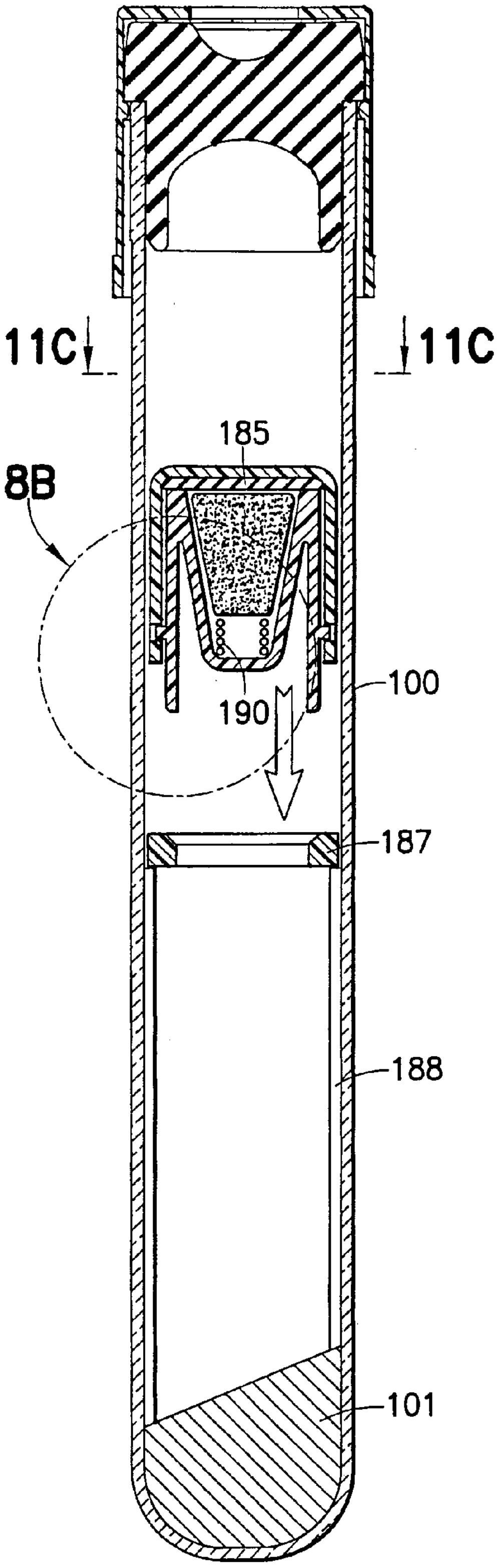
FIG. 11A is a cross-sectional view of an alternate embodiment of a blood collection device of the present invention having a gel separating member.
Figure 11B:
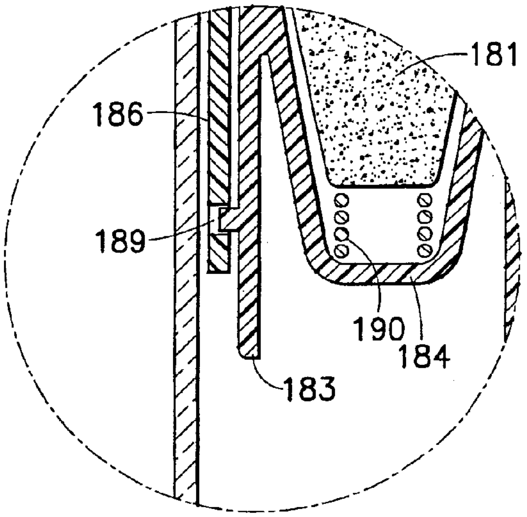
FIG. 11B is a magnified cross-sectional view of the reagent release mechanism of the blood collection device of FIG. 11A before centrifugation.
Figure 11C:
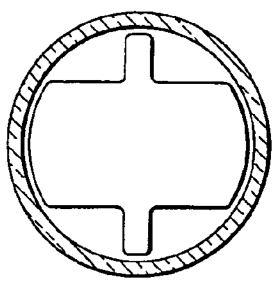
FIG. 11C is a cross-sectional view of the reagent release mechanism of the blood collection device of FIG. 11A from the plane M-M.
Figure 11D:
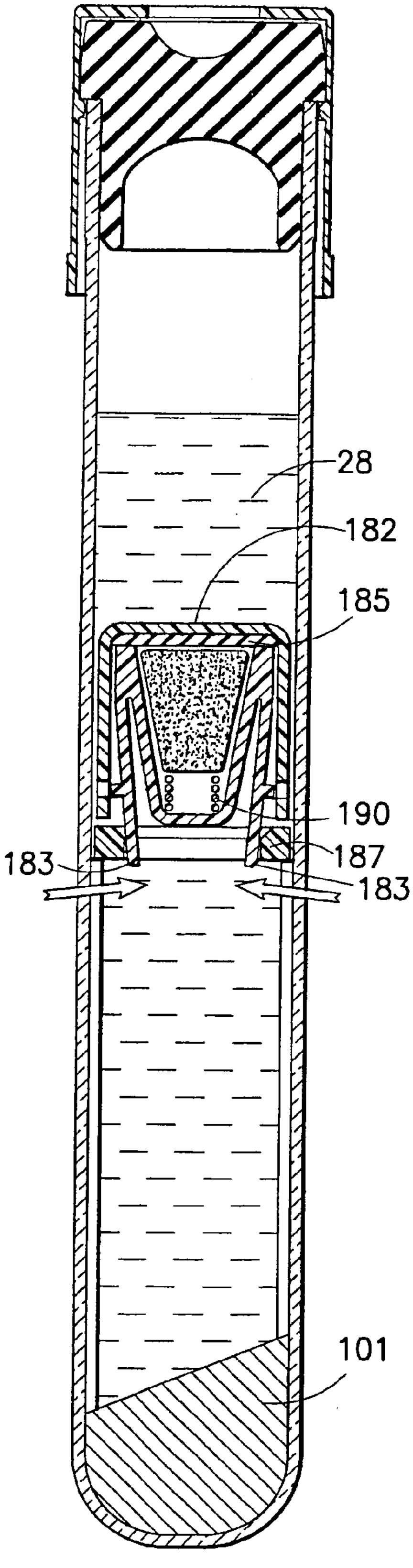
FIG. 11D is a cross-sectional view of the blood collection device of FIG. 11A during centrifugation.
Figure 11E:
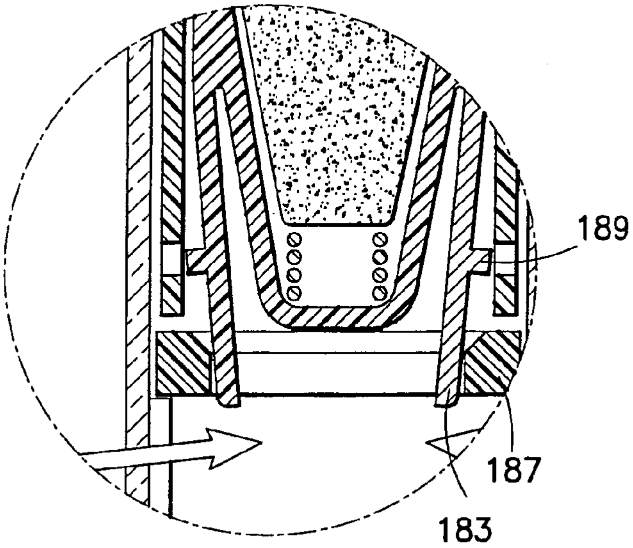
FIG. 11E is a magnified cross-sectional view of the reagent release mechanism of the blood collection device of FIG. 11A during centrifugation.
Figure 11F:
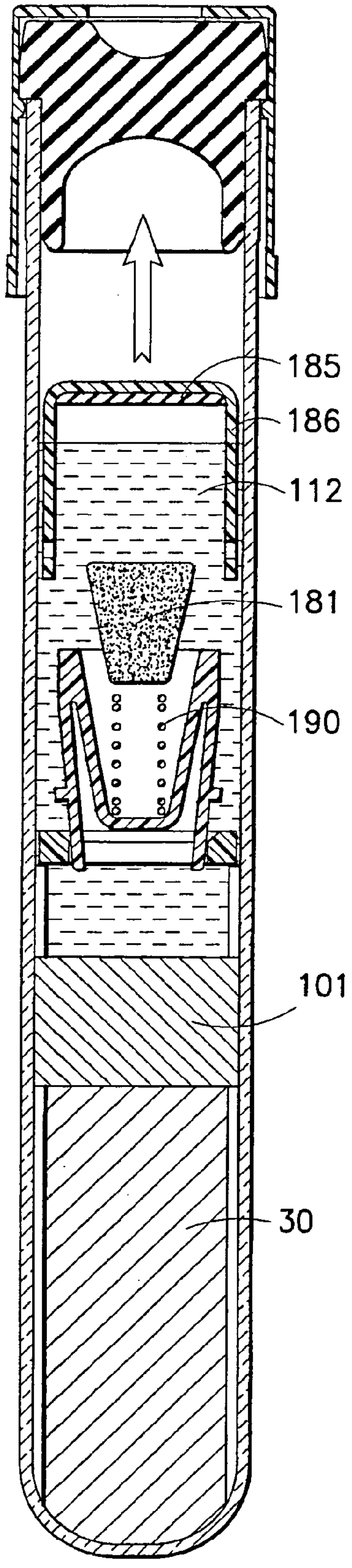
FIG. 11F is a cross-sectional view of the blood collection device of FIG. 11A after centrifugation facilitating separation into its components and activation of the reagent release mechanism.

FIGS. 11A to F show a tube 100 having an open top end and a closed bottom end containing a gel separating member 101. FIGS. 11A, B and C show the embodiment before centrifugation, the reagent 181 contained within a sealed chamber assembly 182 which consists of a cup 184, a seal pad 185 and a cover 186 is formed by snapping two plastic cups together. Two fingers 183 extend from the snap features 189 off the bottom side of the chamber. Integral ribs 188 on the inner surface of the tube support a static cam ring 187. Under centrifugation, FIGS. 11D and E show how the sealed chamber assembly 182 moves down the tube, until the assembly 182 is forced into the static cam ring 187, which then deflects the two fingers 183, thereby freeing the snaps 189 on the chamber assembly 182. When centrifugation is complete, FIG. 11F shows that a small spring 190 within the chamber assembly ejects the reagent tablet 181, the chamber cover 186 and the seal pad 185 into the separated plasma 112.

FIGS. 12A to E show a tube 100 having an open top end and a closed bottom end containing a gel separating member 101.

Figure 12A:
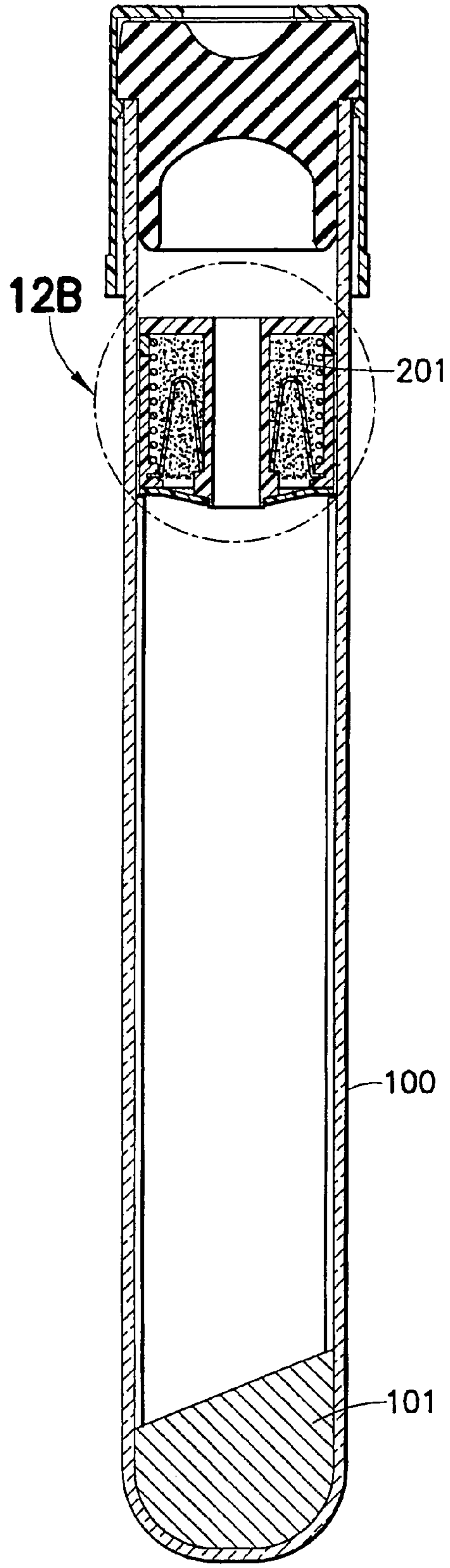
FIG. 12A is a cross-sectional view of an alternate embodiment of a blood collection device of the present invention having a gel separating member.
Figure 12B:
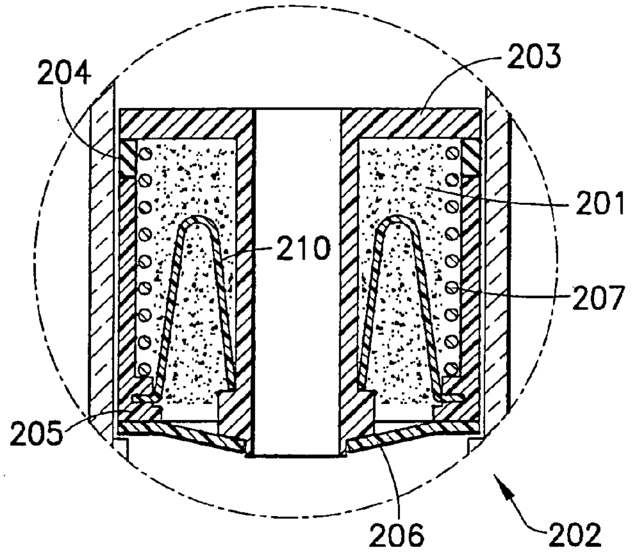
FIG. 12B is a magnified cross-sectional view of the reagent release mechanism of the blood collection device of FIG. 12A before centrifugation.
Figure 12C:
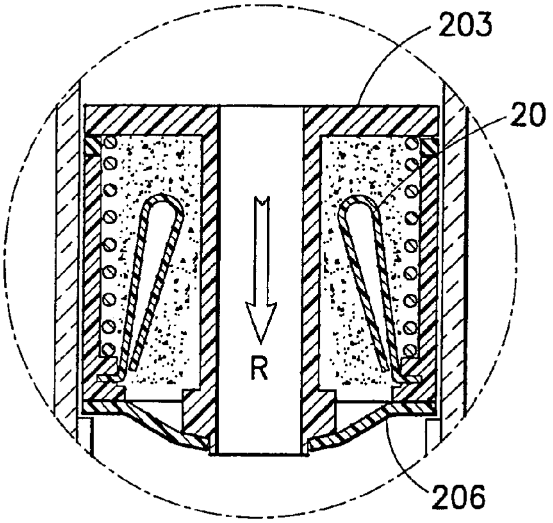
FIG. 12C is a magnified cross-sectional view of the reagent release mechanism of the blood collection device of FIG. 6A during centrifugation.
Figure 12E:
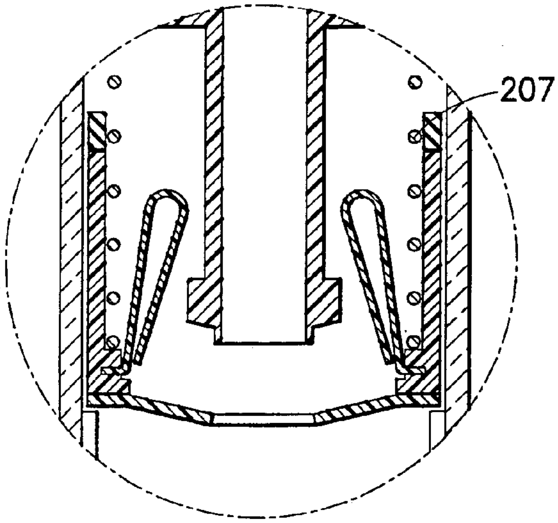
FIG. 12E is a magnified cross-sectional view of the reagent release mechanism of the blood collection device of FIG. 12A after centrifugation.
Figure 12D:
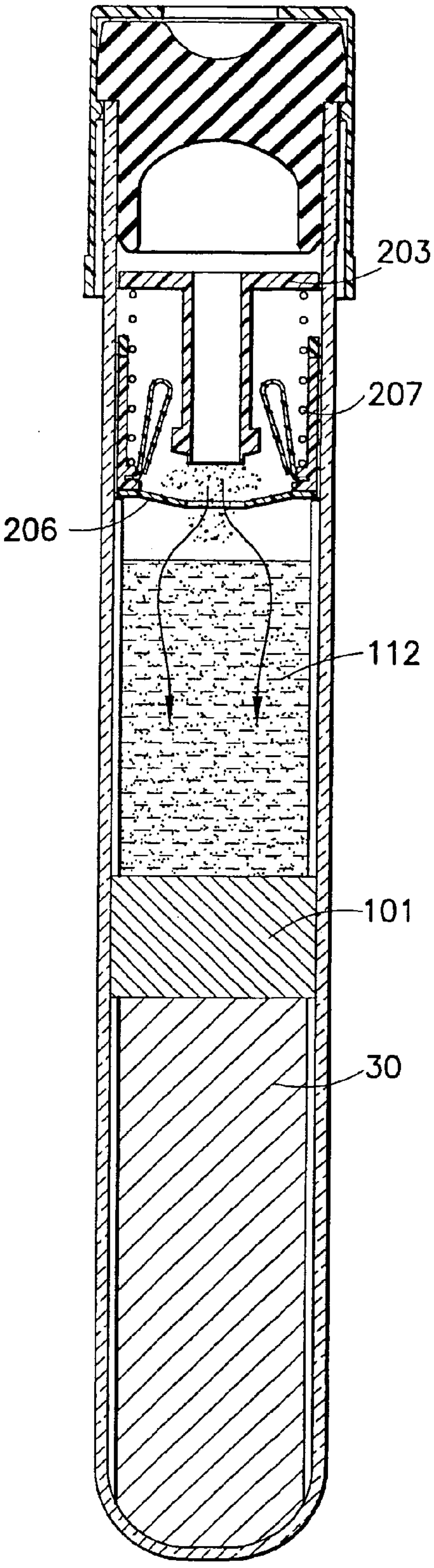
FIG. 12D is a cross-sectional view of the blood collection device of FIG. 6A after centrifugation facilitating separation into its components and activation of the reagent release mechanism.

FIGS. 12A and B show the embodiment before centrifugation, the reagent 201 contained within a sealed chamber assembly 202, which consists of a reagent cup 203, a seal 204 a carrier 205 and an elastomeric washer 206. The reagent cup 203 is spring loaded by spring 207 to lift free from the carrier 205, but is retained by either wire forms or leaf springs 210. Under centrifugation, FIG. 12C shows how the reagent cup 203 is forced down in direction R against the elastomeric washer 206, thereby freeing the leaf springs 210 and letting them retract to their nominal positions. When centrifugation is complete, FIGS. 12D and E show that spring 207 within the chamber assembly 202 lifts the reagent cup 203, allowing the reagent 201 to pass out through the center of the elastomeric washer 206 and into the separated plasma 112.

Figure 13A:
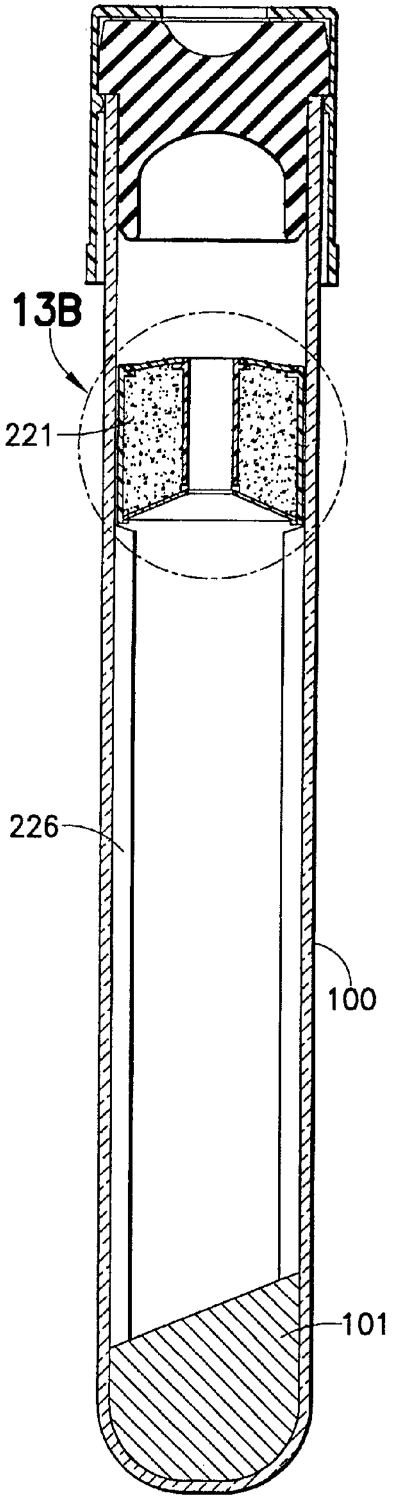
FIG. 13A is a cross-sectional view of an alternate embodiment of a blood collection device of the present invention having a gel separating member.
Figure 13B:
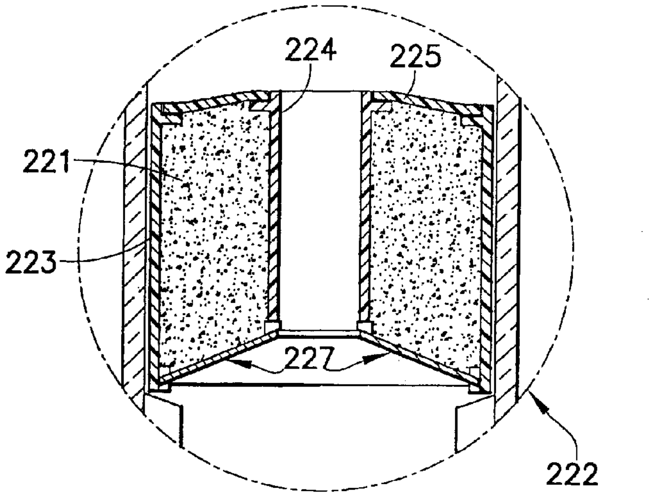
FIG. 13B is a magnified cross-sectional view of the reagent release mechanism of the blood collection device of FIG. 13A before centrifugation.
Figure 13C:
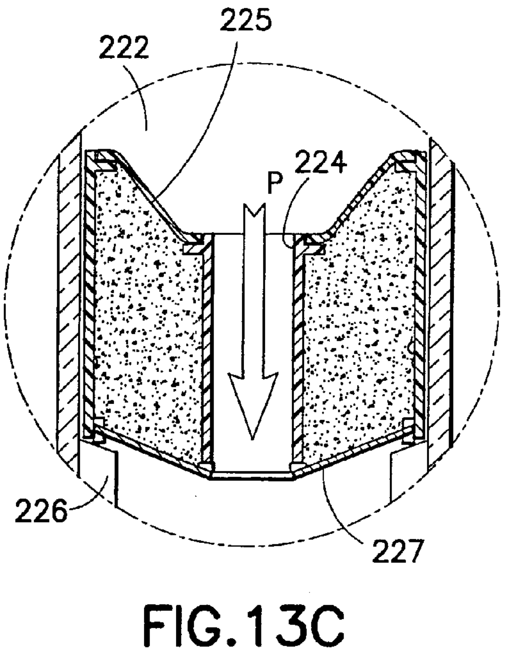
FIG. 13C is a magnified cross-sectional view of the reagent release mechanism of the blood collection device of FIG. 13A during centrifugation.
Figure 13D:
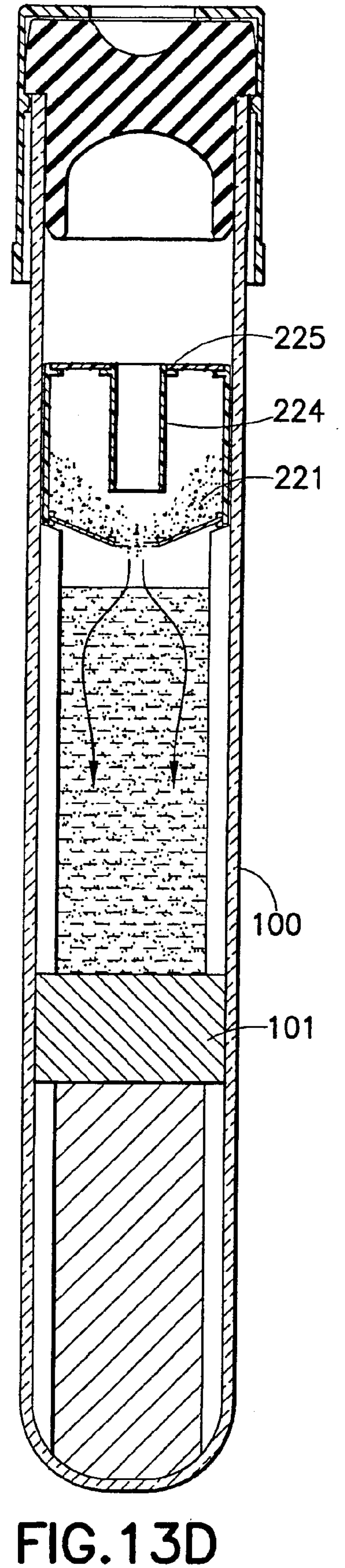
FIG. 13D is a cross-sectional view of the blood collection device of FIG. 13A after centrifugation facilitating separation into its components and activation of the reagent release mechanism.
Figure 13E:
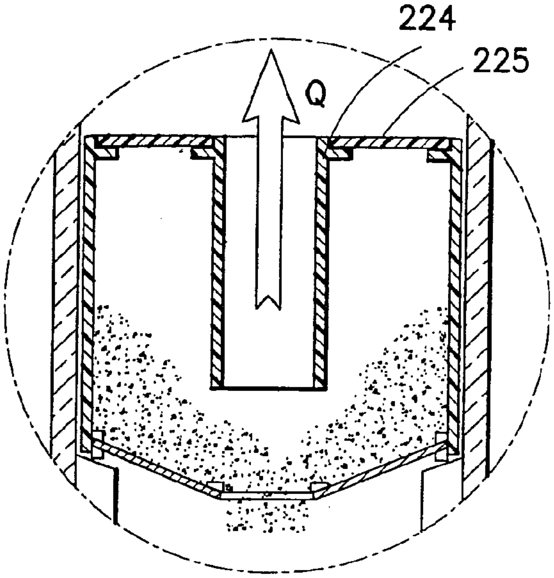
FIG. 13E is a magnified cross-sectional view of the reagent release mechanism of the blood collection device of FIG. 13A after centrifugation.

FIGS. 13A to E show a tube 100 having an open top end and a closed bottom end containing a gel separating member 101. FIGS. 13A and B show the embodiment before centrifugation, the reagent 221 in pellitized form housed within an annular chamber assembly 222, bounded by two plastic cylinders the outer cylinder 223 and pass-through tube 224, with an elastomeric washer 225 affixed to both and enclosing the top of the chamber and a belville washer 227 affixed to the bottom of the outer cylinder 223 and sealed to the pass-through tube 224. FIG. 13C shows how the annular chamber assembly 222 is supported along its outer cylinder circumference by ribs 226 on the inside surface of the tube. During centrifugation, the mass of the pass-through tube 224 forces the belville washer 227 to permanently invert in direction P. This causes elastomeric washer 225 to stretch. FIGS. 13D and E show that the elastomer washer 225 then provides a restoring spring force Q to the pass-through tube 224 when centrifugation is complete opening a pathway for the reagent 221 to enter the plasma.

Figure 14A:
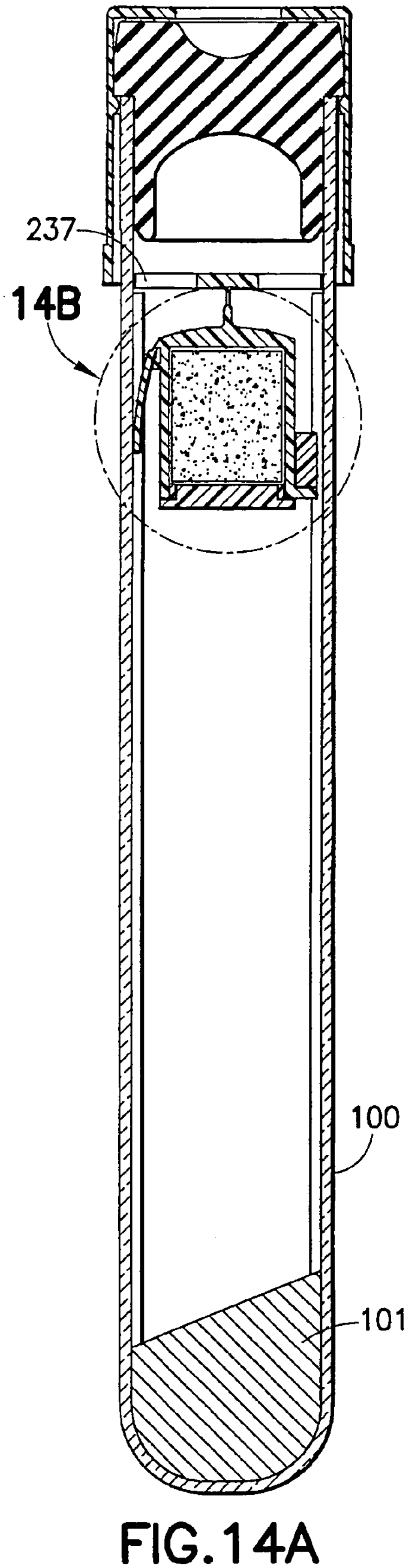
FIG. 14A is a cross-sectional view of an alternate embodiment of a blood collection device of the present invention having a gel separating member.
Figure 14B:
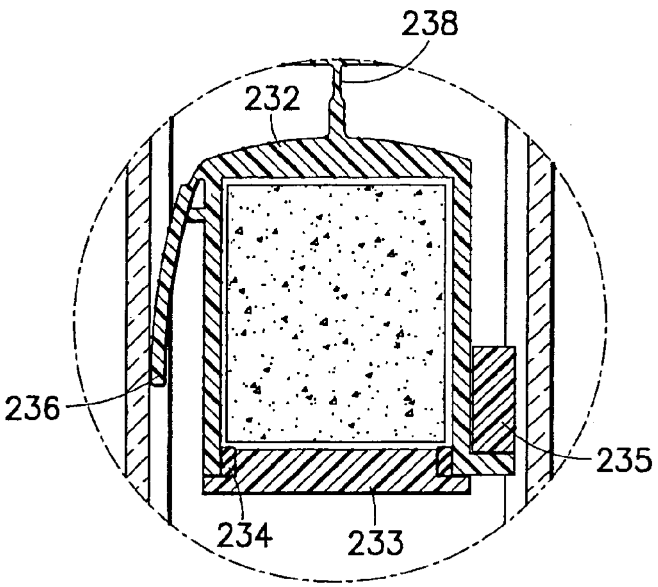
FIG. 14B is a magnified cross-sectional view of the reagent release mechanism of the blood collection device of FIG. 14A before centrifugation.
Figure 14C:
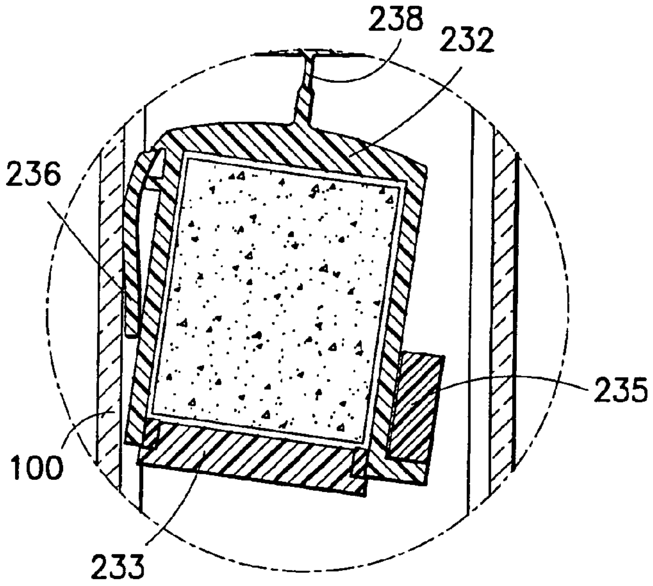
FIG. 14C is a magnified cross-sectional view of the reagent release mechanism of the blood collection device of FIG. 14A during the initial stage of centrifugation.
Figure 14D:
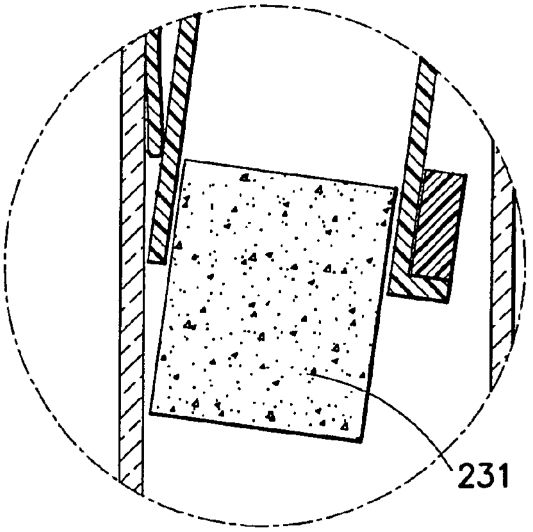
FIG. 14D is a magnified cross-sectional view of the reagent release mechanism of the blood collection device of FIG. 14A during the final stage of centrifugation.
Figure 14E:
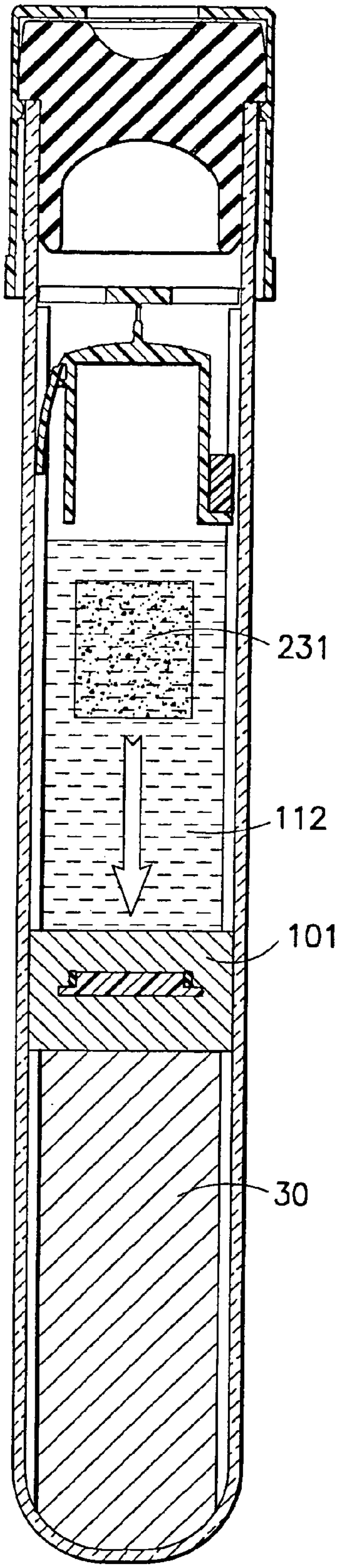
FIG. 14E is a cross-sectional view of the blood collection device of FIG. 14A after centrifugation facilitating separation into its components and activation of the reagent release mechanism.

FIGS. 14A to E show a tube 100 having an open top end and a closed bottom end containing a gel separating member 101. FIGS. 14A and B show the embodiment before centrifugation, the reagent 231 is housed within an inverted cup 232, that is sealed at the bottom open end by a cover plate 233 and seal 234, and attached to a support plate 237 at the top via a living hinge 238. There is a ballast weight 235 attached to one side of the cup 232 and an integrally molded plastic leaf spring 236 is located on the opposite side. FIG. 14C shows how during centrifugation, the eccentric ballast weight 235 causes the cup 232 to rotate about living hinge 238 until it contacts the inner wall of the tube 100 compressing the leaf spring 236. The cover plate 233 launches under the increased gravitational forces of centrifugation and the reagent tablet 231 slides downward. FIG. 14D shows how the reagent tablet 231 is prevented from completely exiting the cup due to the contact with the tube wall. FIG. 14E shows that when centrifugation is complete the leaf spring returns the cup to its nominal position, allowing the reagent tablet 231 to enter the separated plasma 112.

Figure 15A:
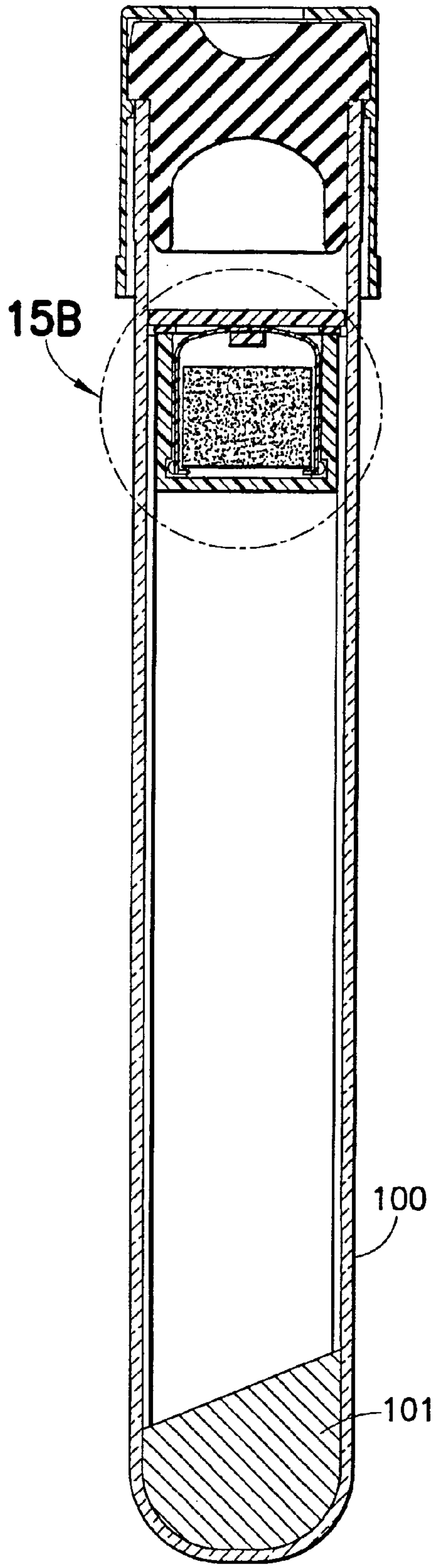
FIG. 15A is a cross-sectional view of an alternate embodiment of a blood collection device of the present invention having a gel separating member.
Figure 15B:
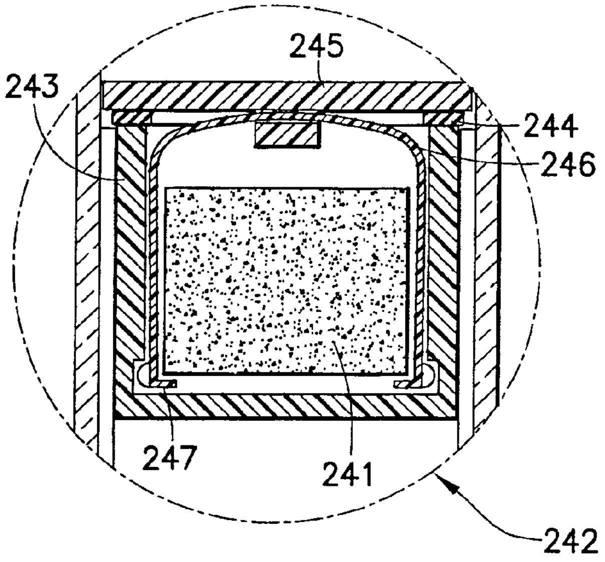
FIG. 15B is a magnified cross-sectional view of the reagent release mechanism of the blood collection device of FIG. 15A before centrifugation.
Figure 15C:
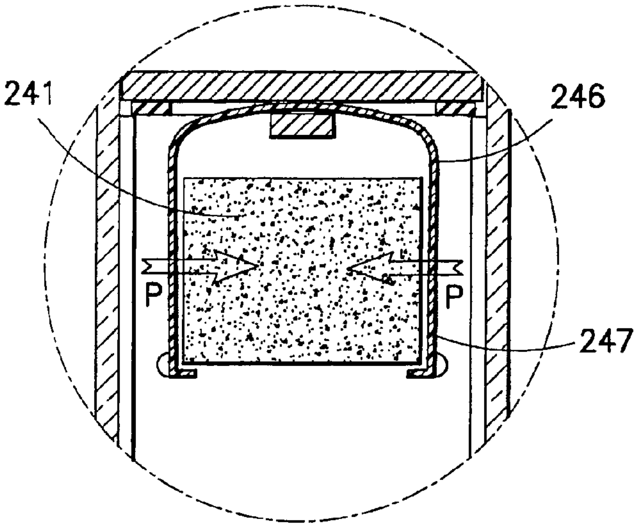
FIG. 15C is a magnified cross-sectional view of the reagent release mechanism of the blood collection device of FIG. 15A during centrifugation.
Figure 15D:
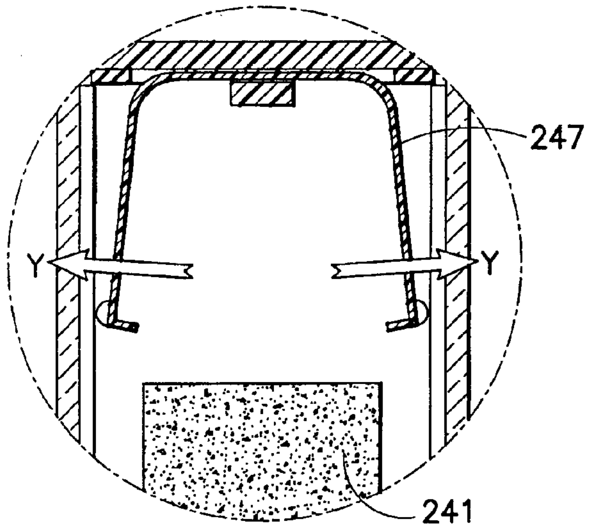
FIG. 15D is a magnified cross-sectional view of the reagent release mechanism of the blood collection device of FIG. 15A after centrifugation.
Figure 15E:
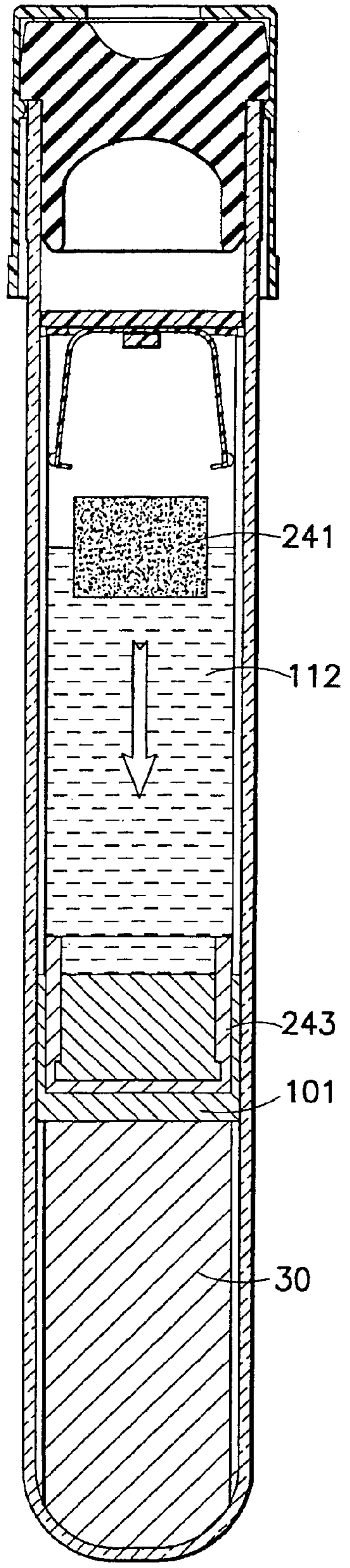
FIG. 15E is a cross-sectional view of the blood collection device of FIG. 15A after centrifugation facilitating separation into its components and activation of the reagent release mechanism.

FIGS. 15A to E show a tube 100 having an open top end and a closed bottom end containing a gel separating member 101. FIGS. 15A and B show the embodiment before centrifugation, the reagent tablet 241 is contained within a chamber assembly 242, that consists of an inverted cup 246, a cover 243 and seal pad 244, and attached to a support plate 245 at the top and is held in place by a spring form. The cover 243 detents to the spring arms 247 and seals 244 to the support plate 245. FIG. 15C shows how under centrifugation, the spring arms 247 deform in the direction of P, therefore cover 243 detaches from the inverted cup 246 and migrates to the gel layer 101, however the reagent tablet 241 is prevented from completely exiting the cup due to the contact with the spring arms 247 which remain in their deflected position as a result of the increased gravitational forces. FIGS. 15D and 15E show that when centrifugation is complete the spring arms 247 open in the direction Y, allowing the reagent tablet 241 to enter the separated plasma 112.

Figure 16A:
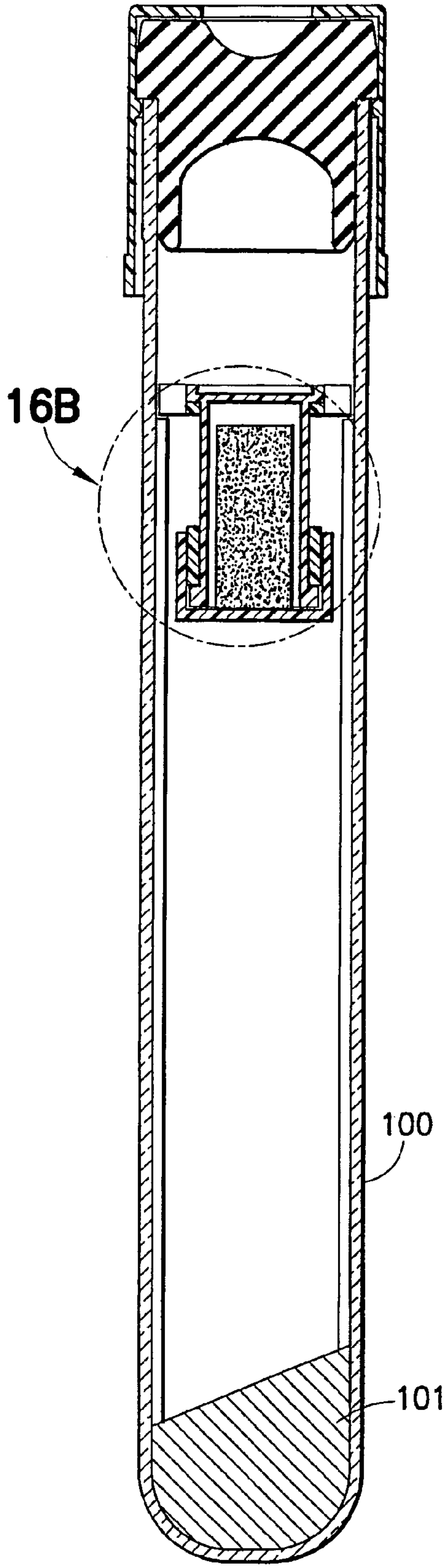
FIG. 16A is a cross-sectional view of an alternate embodiment of a blood collection device of the present invention having a gel separating member.
Figure 16B:
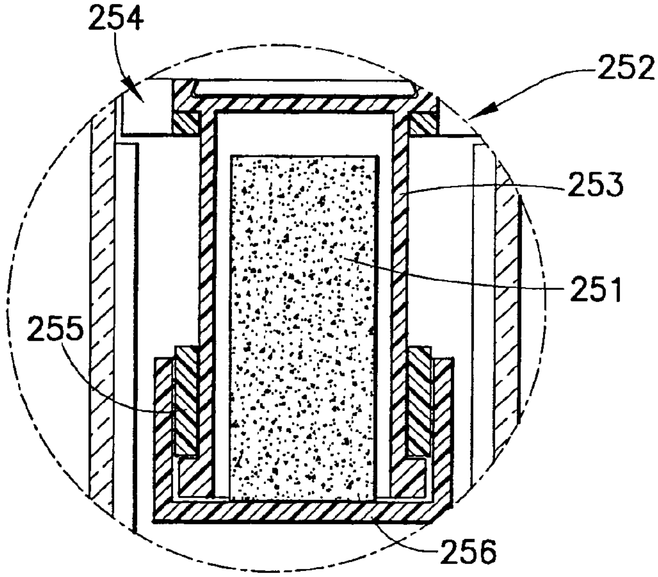
FIG. 16B is a magnified cross-sectional view of the reagent release mechanism of the blood collection device of FIG. 16A.
Figure 16C:
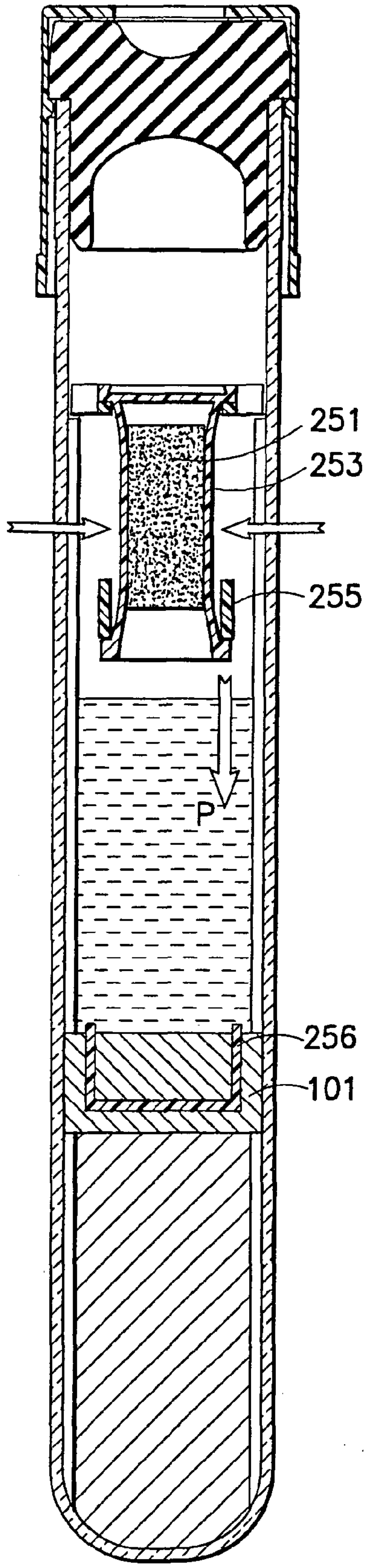
FIG. 16C is a cross-sectional view of the blood collection device of FIG. 16A containing the whole sample during centrifugation.
Figure 16D:
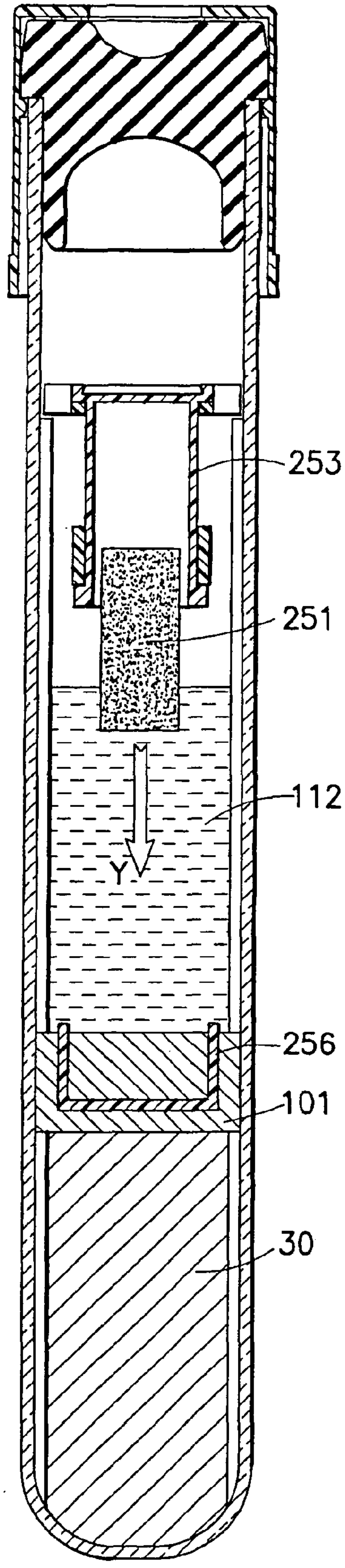
FIG. 16D is a cross-sectional view of the blood collection device of FIG. 16A after centrifugation facilitating separation into its components and activation of the reagent release mechanism.

FIGS. 16A to D show a tube 100 having an open top end and a closed bottom end containing a gel separating member 101. FIGS. 16A and B show the embodiment before centrifugation, the reagent tablet 251 is housed within an elastomer tube assembly 252, that consists of an elastomer tube 253, suspended from a perforated support plate 254, there is also a ballast weight 255 as well as a protective cover 256 which are attached to bottom of the elastomer tube 253. FIG. 16C shows how under centrifugation, the ballast weight 255 causes the elastomer tube 253 to stretch in the direction of P, thereby reducing is diameter and radially gripping the reagent tablet 251. This results in protective cover 256 detaching from the elastomer tube 253 and migrating to the gel layer 101, however the reagent tablet 251 is prevented from completely exiting the elastomer tube 253 due to the radially gripping forces, which exist as a result of the increased gravitational forces. FIGS. 16D shows that when centrifugation is complete the elastomer tube 253 returns to its initial state thereby reducing the radial gripping forces and releasing the reagent tablet 251 into the separated plasma 112.

Figure 17A:
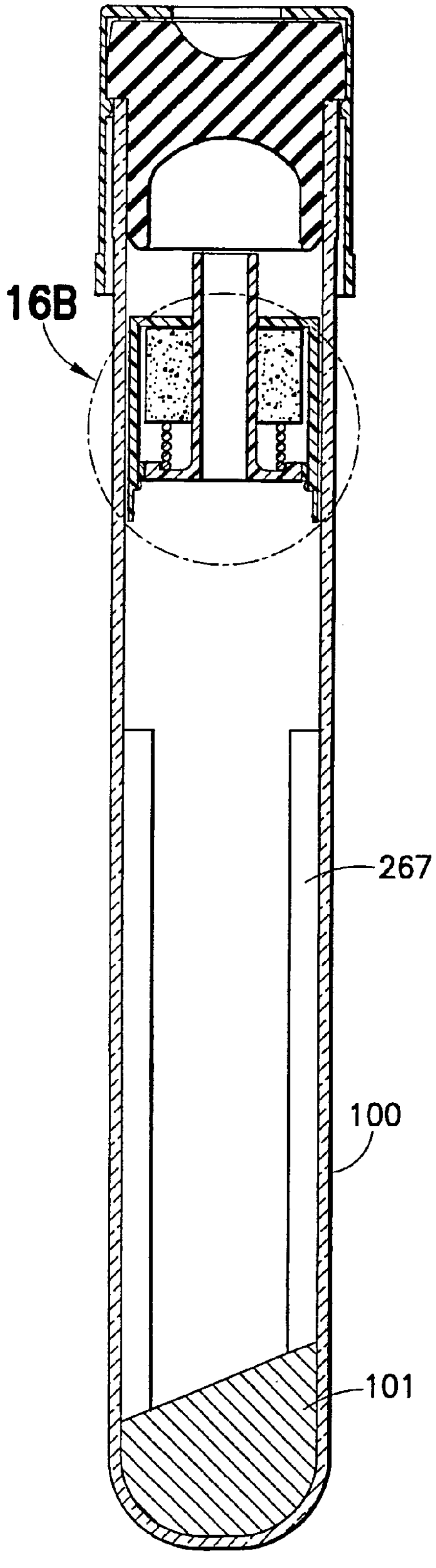
FIG. 17A is a cross-sectional view of an alternate embodiment of a blood collection device of the present invention having a gel separating member.
Figure 17B:
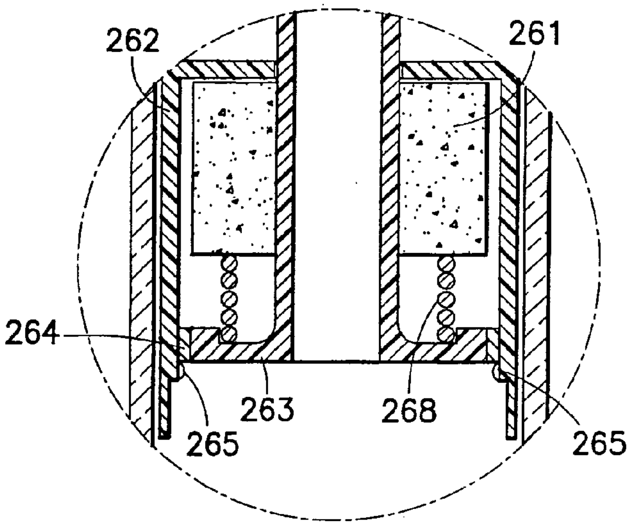
FIG. 17B is a magnified cross-sectional view of the reagent release mechanism of the blood collection device of FIG. 17A.
Figure 17C:
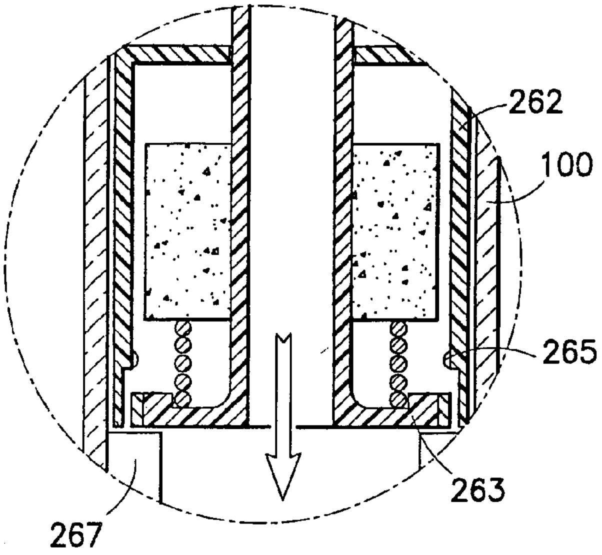
FIG. 17C is a magnified cross-sectional view of the reagent release mechanism of the blood collection device of FIG. 17A during centrifugation.
Figure 17D:
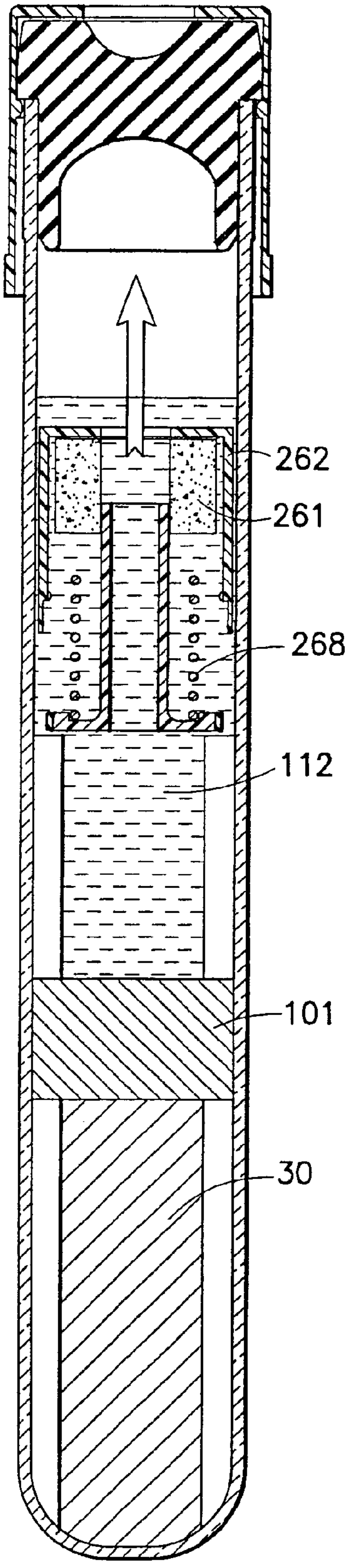
FIG. 17D is a cross-sectional view of the blood collection device of FIG. 17A after centrifugation facilitating separation into its components and activation of the reagent release mechanism.

FIGS. 17A to D show a tube 100 having an open top end and a closed bottom end containing a gel separating member 101. FIGS. 17A and B show the embodiment before centrifugation, the reagent tablet 261 is contained within an inverted cup 262, that is sealed on the lower side by a plate 263 with a seal ring 264 around the periphery. The plate 263 is held in place by detents 265 on the inverted cup 262. FIG. 17C shows how during centrifugation, the inverted cup 262 is drawn down the tube 100 until contact with the support ribs 267 within the tube 100. The increased gravitational forces cause the plate 263 to continue traveling down the tube, freeing it from the detents 265 but preventing the ejection of the inverted cup 262. FIG. 14D shows that when centrifugation is complete the reduced gravitational forces allow the inverted cup 262 and the reagent tablet 261 to be ejected off the plate and into the separated plasma 112 by a small compression spring 268.

Figure 18A:
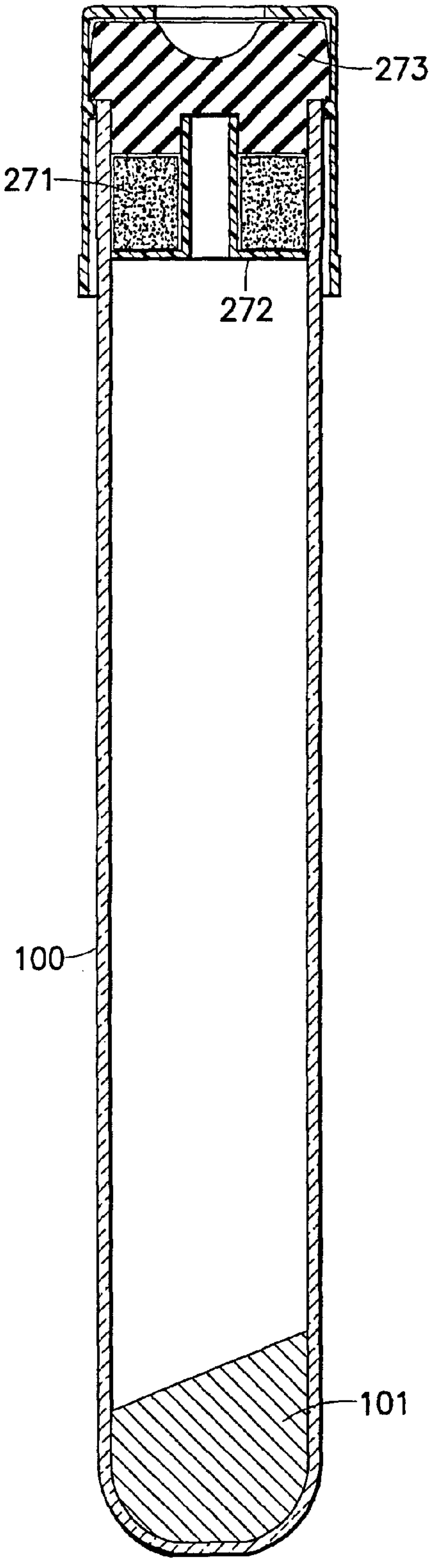
FIG. 18A is a cross-sectional view of an alternate embodiment of a blood collection device of the present invention having a gel separating member.
Figure 18B:
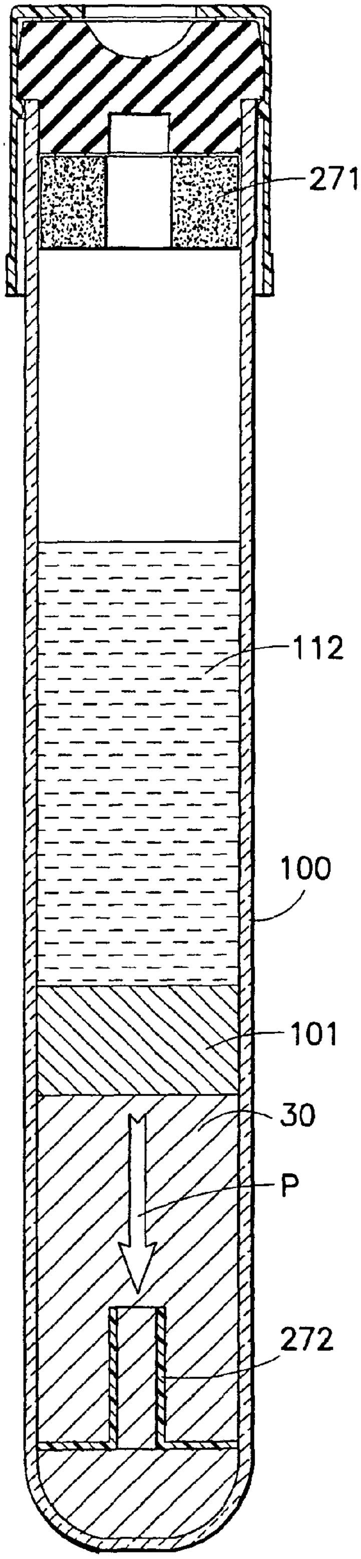
FIG. 18B is a cross-sectional view of the blood collection device of FIG. 18A after centrifugation facilitating separation into its components and activation of the reagent release mechanism.

FIGS. 18A and B show a tube 100 having an open top end and a closed bottom end containing a gel separating member. FIG. 18A shows the embodiment before centrifugation, the reagent tablet 271, is contained within a reagent cup 272 and is affixed to the inner diameter of the tube 100 adjacent to the open end of the tube and/or to the underside of the tube closure 273. FIG. 18B shows how during centrifugation, the reagent cup 272 migrates down the tube 100 in the direction of P to the bottom of the tube 100 and becomes located below the gel layer 101 whereas the reagent tablet 271 remains affixed to the inner diameter of the tube 100 adjacent to the open end of the tube and/or to the underside of tube closure 273. The exposed reagent 271 is then mixed with the separated plasma 112 by a simple inversion of the tube.

Figure 19A:
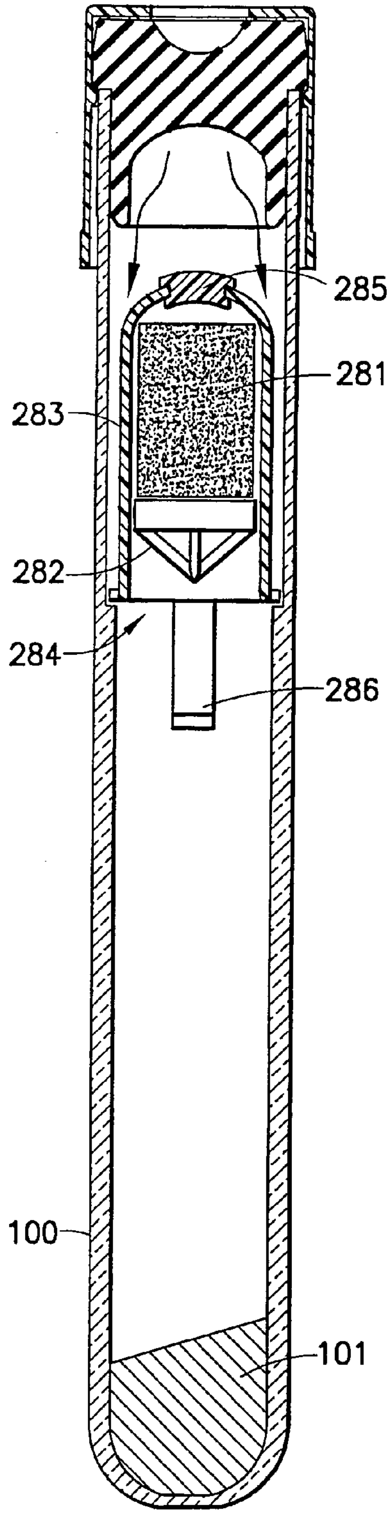
FIG. 19A is a cross-sectional view of an alternate embodiment of a blood collection device of the present invention having a gel separating member.
Figure 19B:
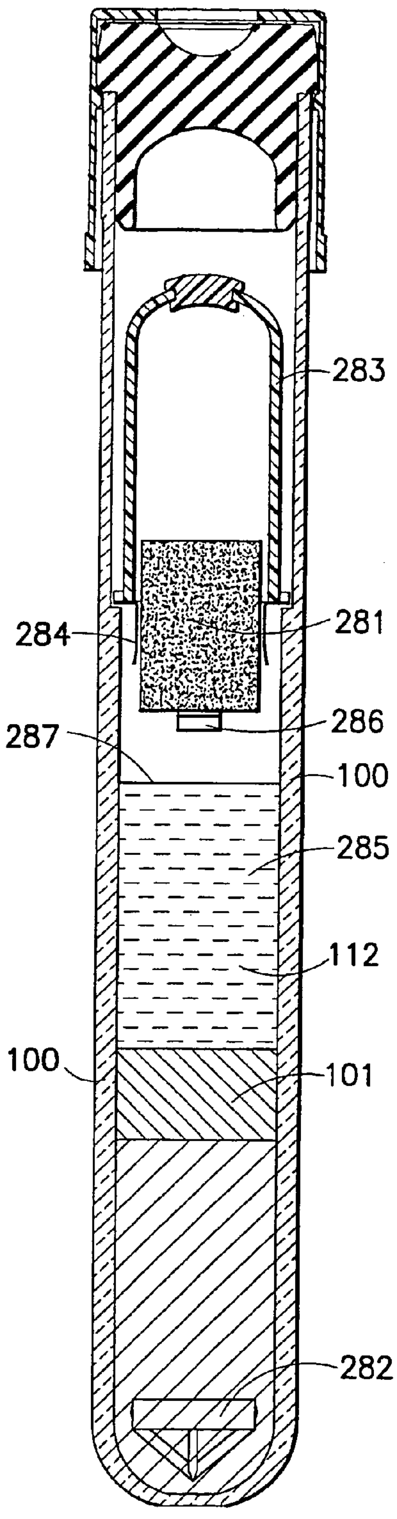
FIG. 19B is a cross-sectional view of the blood collection device of FIG. 19A after centrifugation facilitating separation into its components and activation of the reagent release mechanism.

FIGS. 19A and B show a tube 100 having an open top end and a closed bottom end containing a gel separating member. FIG. 19A shows the embodiment before centrifugation, the reagent tablet 281 and a plastic arrowhead 282 are contained within a capsule 283, which is at a fixed location within the tube 100. A septum 285 for post centrifugation sample access is located at the top while a foil barrier 284 seals the base of capsule 283. FIG. 19B shows how during centrifugation, the plastic arrowhead 282 pierces the foil barrier 284 migrates down to the bottom of the tube 100 and becomes located below the gel layer 101, the reagent tablet 281 then drops down and partially out of the capsule 283 and is retained above the plasma fluid level 287 by three retaining fingers 286 which are integral to the capsule 283 and protruding below the foil barrier 284. The exposed reagent tablet 281 is then mixed with the separated plasma 112 by a simple inversion of the tube 100.

Figure 20A:
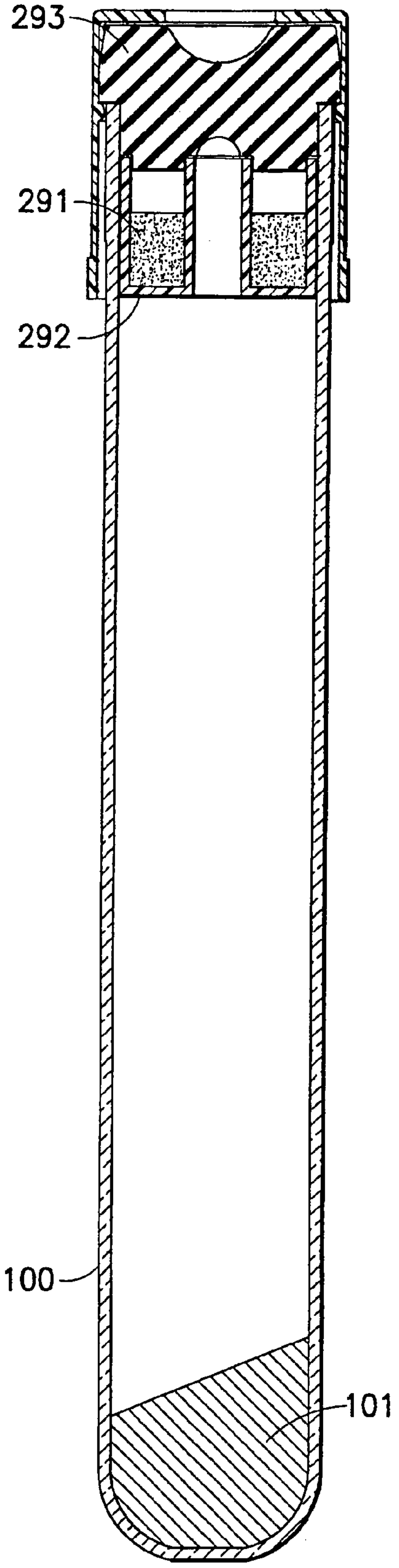
FIG. 20A is a cross-sectional view of an alternate embodiment of a blood collection device of the present invention having a gel separating member.
Figure 20B:
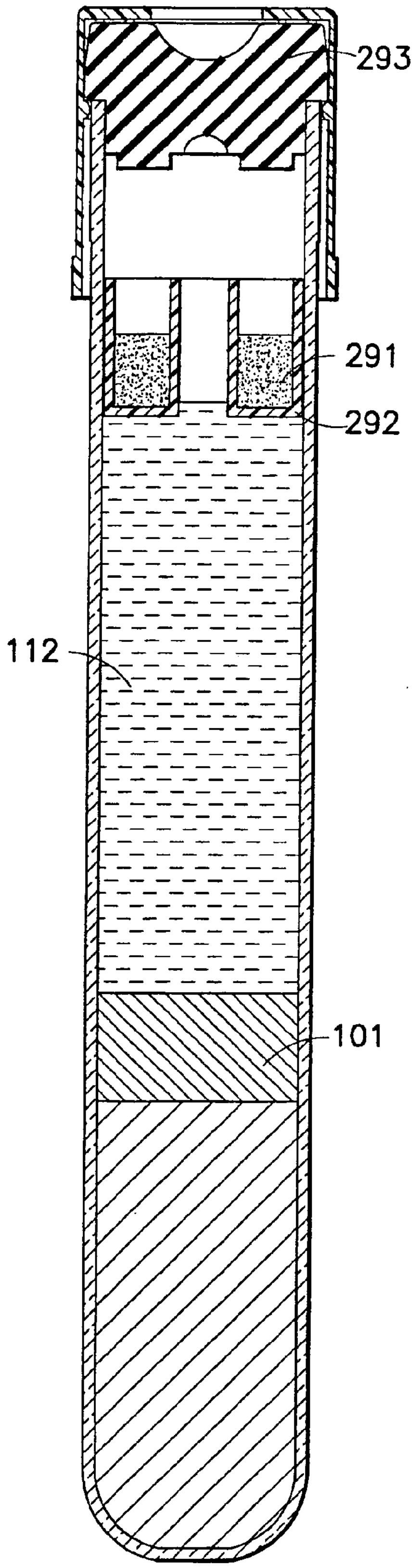
FIG. 20B is a cross-sectional view of the blood collection device of FIG. 20A after centrifugation facilitating separation into its components and activation of the reagent release mechanism.
Figure 20C:
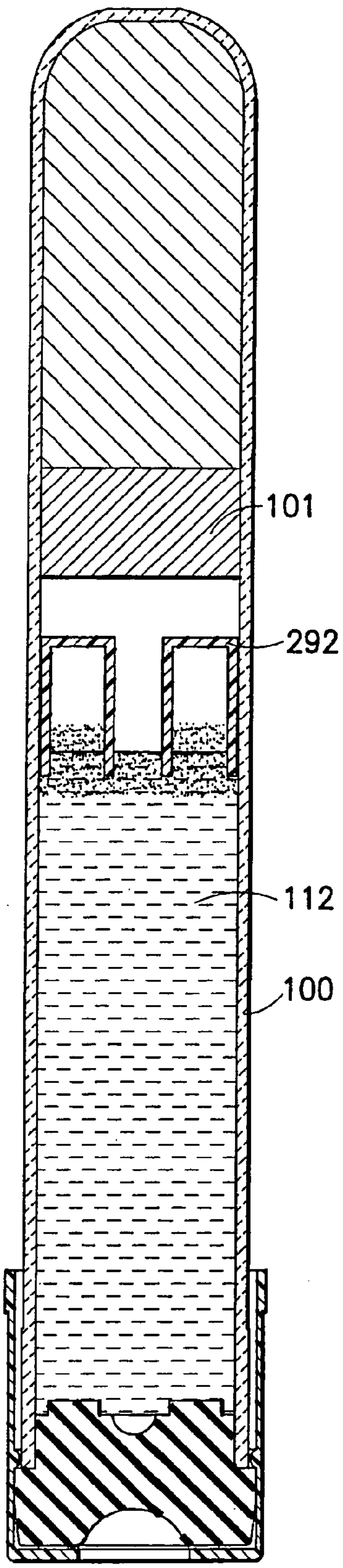
FIG. 20C is a cross-sectional view of the blood collection device of FIG. 20A after centrifugation, inverted through 180 degrees, facilitating mixing of the reagent with the desired discrete component.
Figure 20D:
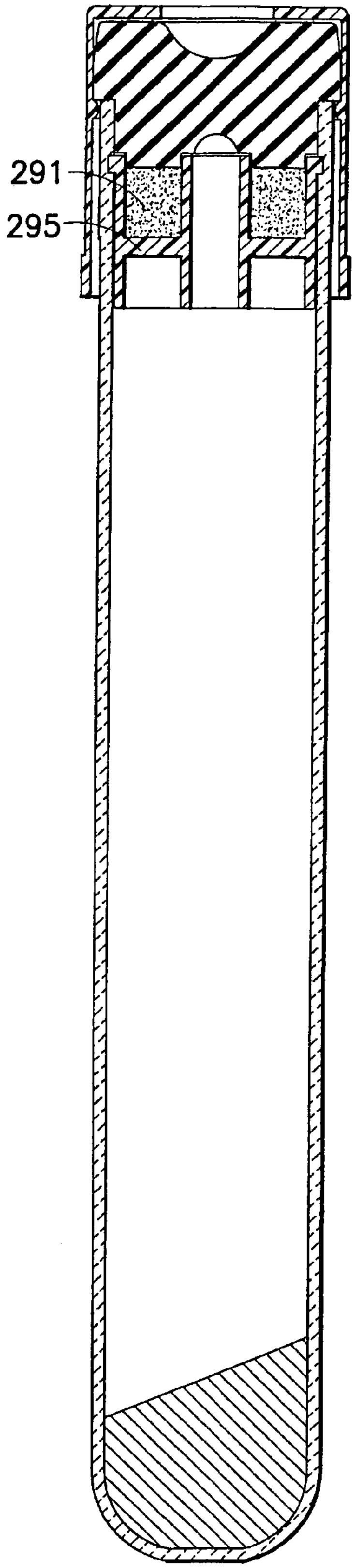
FIG. 20D is a cross-sectional view of an alternate embodiment of a blood collection device of the FIG. 20A having a gel separating member.

FIGS. 20A to D show a tube 100 having an open top end and a closed bottom end containing a gel separating member 101. FIGS. 20A shows the embodiment before centrifugation, the reagent 291 is contained within a reagent cup 292, which mates with and is sealed by the underside of the tube enclosure 293. FIG. 20B shows how during centrifugation, the reagent cup 292 launches free from the tube enclosure 293 and floats on the surface of the plasma 112. FIG. 20C shows that when centrifugation is complete, an inversion of the tube 100 causes the reagent cup 292 to float toward the gel layer 101, emptying the reagent 291 into the separated plasma 112. FIGS. 20D shows an alternate embodiment of the design of the reagent cup 295, before centrifugation.

Figure 21A:
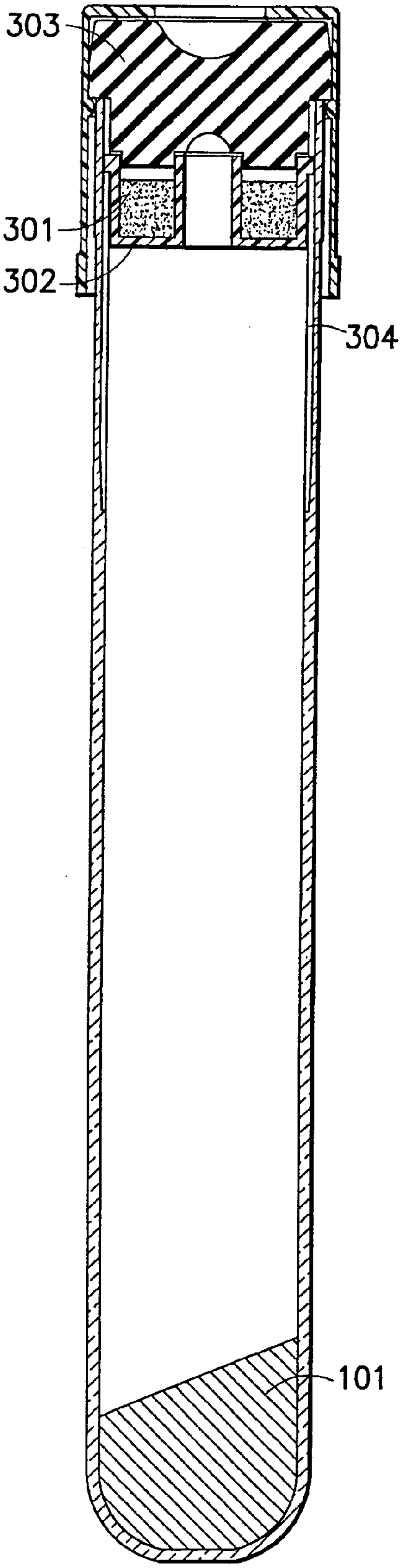
FIG. 21A is a cross-sectional view of an alternate embodiment of a blood collection device of the present invention having a gel separating member.
Figure 21B:
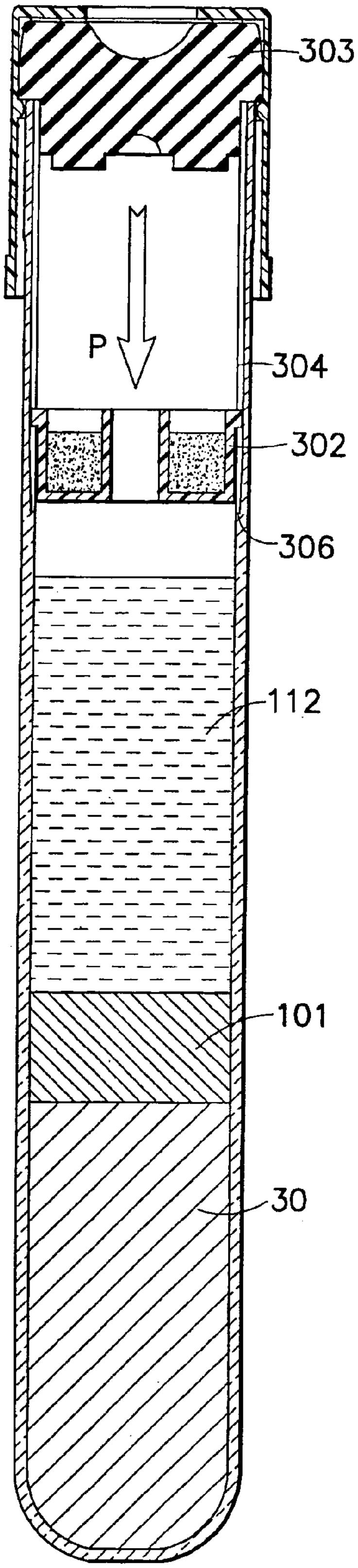
FIG. 21B is a cross-sectional view of the blood collection device of FIG. 21A after centrifugation facilitating separation into its components and activation of the reagent release mechanism.

FIGS. 21A and B show a tube 100 having an open top end and a closed bottom end containing a gel separating member 101. FIGS. 21A shows the embodiment before centrifugation, the reagent 301 is contained within a reagent cup 302, which sealed by the underside of the tube enclosure 303. FIG. 21B shows how during centrifugation, the reagent cup 302 detaches from the tube enclosure 303 and slides down tracks 304 in the tube inner wall in the direction of P. The tracks 304 are slightly tapered to create an interference fit with the reagent cup 302, which holds the reagent cup 302 in the displaced position 306. The exposed reagent tablet 301 is then mixed with the separated plasma 112 by a simple inversion of the tube 100.

Figure 22A:
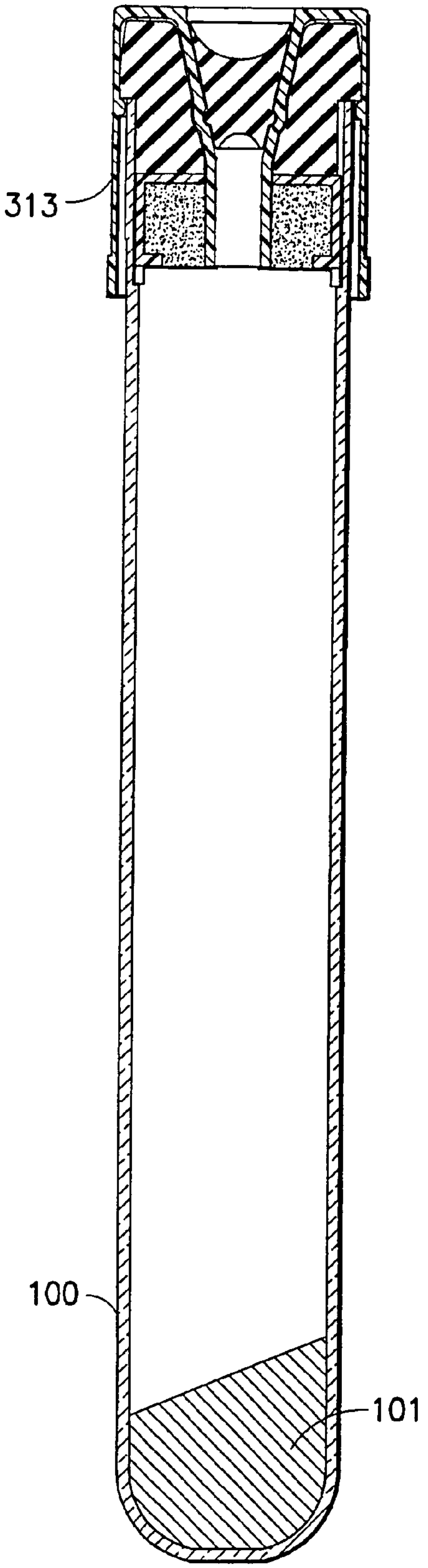
FIG. 22A is a cross-sectional view of an alternate embodiment of a blood collection device of the present invention having a gel separating member.
Figure 22B:
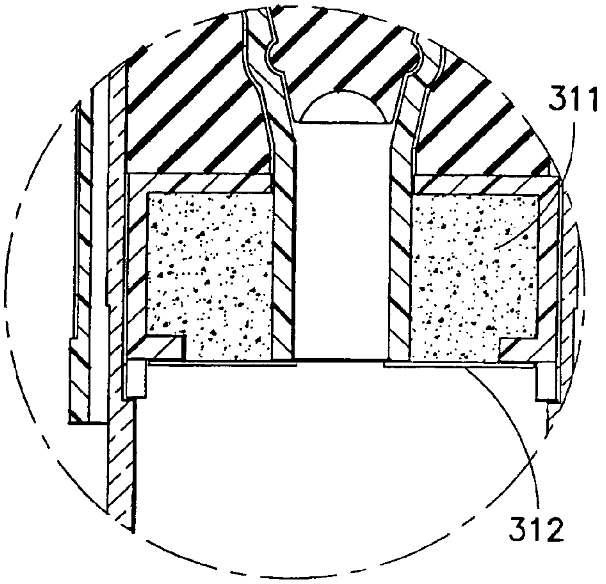
FIG. 22B is a magnified cross-sectional view of the reagent release mechanism of the blood collection device of FIG. 22A.
Figure 22C:
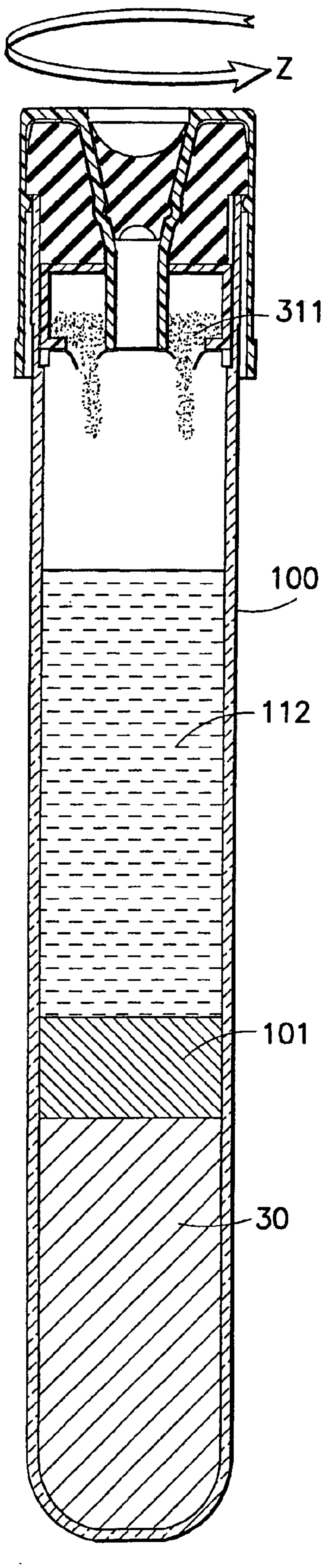
FIG. 22C is a cross-sectional view of the blood collection device of FIG. 22A after centrifugation facilitating separation into its components and activation of the reagent release mechanism.

FIGS. 22A to C show a tube 100 having an open top end and a closed bottom end containing a gel separating member 101. FIGS. 22A and B show the embodiment before centrifugation, the reagent 311 is contained behind a thin tear away seal 312, which is attached to the inner wall of the tube 100 and to the cap 313. FIG. 22C shows that when centrifugation is complete, the cap 313 is rotated in the direction Z, tearing the seal 312 and allowing the reagent 311 to mix with the separated plasma 112.

As reflected in the above embodiments, the reagent release mechanisms generally function by (but are not limited to);

(a) A bias element (such as a spring or belleville washer), holding the reagent release mechanism closed; the separation process (e.g. centrifugation) overcomes the bias and allows contact with the reagent after separation (passive);

(b) A breakable or puncturable pouch/compartment capable of being manually opened after separation (manual).

(c) A container attached to the tube closure, where this attachment to the closure holds the reagent release mechanism closed; the separation process (e.g. centrifugation) overcomes the attachment force, releasing the container and allowing contact with the reagent after separation (passive);

or (d) A container attached to a cover, where the cover prevents contact with the reagent; the separation process (e.g. centrifugation) overcomes the attachment force, releasing the cover and allowing contact with the reagent after separation.

Note that some combination of passive and manual is possible, e.g. where the separation process releases a locking mechanism, but a manual step is required to open a container or passage.

As reflected in the above embodiments, the reagent release mechanism is generally located (but is not limited to);

(a) Attached directly to the tube closure.

(b) Adjacent to the tube enclosure, e.g. resting on a structural member located near the closure.

(c) A position in the tube adjacent to but above the final position of the separating member resting on a structural member such as a rib integral with the inner wall of the tube.

The device of the present invention may comprise a variety of tube coatings or the addition of other compounds to the stabilizing agent. In one alternate embodiment, a spray-dried anticoagulant formulation may be coated on the interior of the container to interact with the whole blood sample. After blood is collected in the device of the present invention, a cascade reaction may occur that causes the blood to clot. Anticoagulants are materials that are used to prevent the clotting of blood by blocking the cascade mechanism that causes clotting. To collect a plasma sample from whole blood, an anticoagulant is typically added immediately to preserve the integrity of the sample. There are commercially available tubes for plasma collection that contain numerous types of anticoagulants, such as sodium citrate, heparin, potassium EDTA and the like. The selection of the type of anticoagulant used may be selected to avoid interference with bDNA, PCR, or other amplification techniques used in nucleic acid testing. Commercially available blood collection tubes suitable for obtaining plasma/serum include the following, all of which are sold by Becton, Dickinson and Company, Franklin Lakes, N.J., with all registrations and trademarks belonging to Becton, Dickinson and Company: VACUTAINER® hematology tubes, catalog nos. 367650-1, 367661, 6405, 6385, 6564, 367653, 367665, 367658, 367669, 6450-8, 6535-37 and 367662; VACUTAINER® $K_2$EDTA tubes, catalog nos. 367841-2, 367856 and 367861; VACUTAINER® PST tubes, catalog nos. 367793-4, 6698, 6595 and 6672; VACUTAINER® CPT tubes, catalog nos. 362753 and 362760-1; VACUTAINER® SST tubes, catalog nos. 367782-89, 6509-17 and 6590-92; and VACUTAINER® ACD tubes catalog nos. 367756, 364012 and 4816.

The device of the present invention may be used to collect and prepare a specimen for nucleic acid testing. First, a specimen such as a whole blood sample or a pretreated cell fraction of blood is collected into the prepared tube, while maintaining the whole blood sample separate from a stabilizing agent located within the tube. Next, the tube is centrifuged to induce separation of plasma from the red and white blood cells and platelets such that the separating member migrates to a point intermediate to the denser white and red blood cells and platelets and the less dense plasma fraction of the blood sample, thereby facilitating isolation and subsequent removal of the plasma. The plasma in the tube moves into contact and is mixed with the nucleic acid stabilizing agent, for example by manual inversion of the tube.

The present invention could be used by pharmaceutical companies, biotechnology companies, contract research organizations, university researchers, research hospitals and any institution or individual who is interested in studying nucleic acids. The present invention would enable researchers to conveniently and readily protect and process plasma samples for downstream analysis without necessitating refrigeration for storage or shipping. Moreover it is possible to use the invention with any agent, which one wishes to bring in contact with only selected components of blood.

Additionally, the assembly of the present invention does not require any additional steps or treatment by a medical practitioner; and the blood or fluid sample can be drawn in the standard fashion, using standard sampling equipment.

It should be noted that in each embodiment a mechanical separator could be used interchangeably where a gel separator is shown and vice versa. Also wherever the term plasma is mentioned, any separated component of blood such as serum could also apply and vice versa.

What is claimed is:

1. A device for collecting a biological sample, comprising:

a container having a first open end, and a closed bottom end;

a separating member disposed in the container, the member capable of separating the sample into discrete components;

at least one reagent release mechanism comprising a sealed chamber positioned above the separating member; and at least one reagent located within the sealed chamber of the reagent release mechanism; wherein the reagent release mechanism prevents contact between the reagent and the biological sample until after centrifugation and separation of the biological sample into discrete components, wherein activation of the reagent release mechanism unseals the chamber and allows the reagent to contact the discrete component.

2. The device of claim 1, wherein the separating member is located at the closed bottom end.

3. The device of claim 1, wherein the separating member is located intermediate of the top and bottom ends.

4. The device of claim 1, wherein the reagent release mechanism is located at the first open end.

5. The device of claim 1, wherein the container is a tube having a closure in the first open end.

6. The device of claim 5, wherein the reagent release mechanism is secured to the closure.

7. The device of claim 5, wherein the reagent release mechanism is supported by an integral structural member on the inside walls of the tube.

8. The device of claim 7, wherein the structural member comprises integral ribs.

9. The device of claim 5, wherein the tube is evacuated to a pressure lower than atmospheric pressure.

10. The device of claim 1, wherein the reagent is a nucleic acid stabilizing agent.

11. The device of claim 10, wherein the nucleic acid stabilizing agent is positioned to selectively contact a plasma or serum component separated from the whole blood.

12. The device of claim 1, wherein the separating member is a mechanical separating element.

13. The device of claim 1, wherein the separating member is a gel.

14. The device of claim 13, wherein the gel separating member is physically separated from the reagent.

15. The device of claim 1, wherein the separating member has a density intermediate of plasma and remaining cellular components, or intermediate of serum and red blood cells.

16. The device of claim 1, wherein the separating member is a filter.

17. The device of claim 1, wherein the reagent is in a form selected from the group consisting of a solution, suspension or other liquid, a pellet, a tablet, a capsule, a spray-dried material, a freeze-dried material, a powder, a particle, a gel, crystals or a lyophilized material.

18. The device of claim 1 wherein the reagent is a protein stabilizer.

19. The device of claim 1, wherein activation of the reagent release mechanism allows the reagent to contact the desired discrete component of the separated biological sample while remaining free of contact with undesired components.

20. The device of claim 1, wherein the reagent release mechanism comprises a passive activation system.

21. The device of claim 20, wherein the reagent release mechanism allows the reagent to contact the discrete component by disengagement of a cover from the reagent release mechanism assembly.

22. The device of claim 20, wherein the reagent release mechanism allows the reagent to contact the discrete component by the opening of a reagent exit doorway in the release mechanism assembly.

23. The device of claim 1, wherein the reagent release mechanism is activated by centrifugation of the biological sample.

24. The device of claim 1, wherein the reagent release mechanism is activated by a manual act after the separation of the biological sample.

25. The device of claim 1, wherein the container further comprises an anticoagulant.

* * * * *